(12) United States Patent  
Dwarakanath et al.

(10) Patent No.: US 10,168,265 B2  
(45) Date of Patent: Jan. 1, 2019

(54) PORTABLE APPARATUS AND METHODS FOR ANALYZING INJECTION FLUIDS

(71) Applicant: Chevron U.S.A. Inc., San Ramon, CA (US)

(72) Inventors: Varadarajan Dwarakanath, Houston, TX (US); Dustin L. Walker, Houston, TX (US); David R. Espinosa, Houston, TX (US); Dennis A. Alexis, Richmond, TX (US); Harold C. Linnemeyer, Sugar Land, TX (US); Marlon Solano, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 15/996,040

(22) Filed: Jun. 1, 2018

(65) Prior Publication Data

US 2018/0275036 A1 Sep. 27, 2018

Related U.S. Application Data

(63) Continuation of application No. 15/661,914, filed on Jul. 27, 2017.

(Continued)

(51) Int. Cl.
*E21B 43/16* (2006.01)
*E21B 43/26* (2006.01)
(Continued)

(52) U.S. Cl.
CPC .............. *G01N 11/00* (2013.01); *E21B 43/16* (2013.01); *E21B 43/26* (2013.01); *E21B 47/00* (2013.01);

(Continued)

(58) Field of Classification Search
CPC ......... E21B 43/26; E21B 43/16; G01N 11/00; G01N 2011/006; G01L 13/00; B01D 2101/04; B01D 24/4884
See application file for complete search history.

(56) References Cited

U.S. PATENT DOCUMENTS 2,826,060 A * 3/1958 Gordon .................. G01N 11/04
73/54.12
3,502,220 A * 3/1970 Kohlberg ............... B01D 35/02
210/416.1
(Continued)

FOREIGN PATENT DOCUMENTS

WO 2012/140092 A1 10/2012
WO 2016/046585 A1 3/2016
(Continued)

OTHER PUBLICATIONS

Dictionary definition of "housing", accessed via www.thefreedictionary.com on Aug. 20, 2018.*
(Continued)

*Primary Examiner* — Blake E Michener

(57) ABSTRACT

Provided herein are portable apparatus as well as methods of analyzing an injection fluid using these portable apparatus. In some embodiments, the injection fluid can contain a polymer, but a polymer is not necessary. For example, the portable apparatus and methods may be used to determine viscosity, long term injectivity, filter ratio, or any combination thereof of the injection fluid.

20 Claims, 15 Drawing Sheets

US 10,168,265 B2
Page 2

Related U.S. Application Data

(60) Provisional application No. 62/431,352, filed on Dec. 7, 2016, provisional application No. 62/367,567, filed on Jul. 27, 2016.

(51) Int. Cl.
*E21B 47/00* (2012.01)
*G01L 13/00* (2006.01)
*G01N 11/00* (2006.01)

(52) U.S. Cl.
CPC .......... *G01L 13/00* (2013.01); *B01D 2101/04* (2013.01); *G01N 2011/006* (2013.01)

(56) References Cited

U.S. PATENT DOCUMENTS

| | | | | |
|---|---|---|---|---|
| 3,773,438 | A * | 11/1973 | Hall | E21B 43/26 417/345 |
| 3,957,637 | A * | 5/1976 | Morey | B01D 24/002 210/741 |
| 4,534,869 | A * | 8/1985 | Seibert | B01D 36/04 210/241 |
| 4,700,567 | A * | 10/1987 | Frey | E21B 43/26 73/152.39 |
| 4,850,750 | A * | 7/1989 | Cogbill | B01F 13/0035 406/82 |
| 4,901,563 | A * | 2/1990 | Pearson | B01F 15/00207 166/308.1 |
| 5,257,528 | A * | 11/1993 | Degouy | E21B 49/005 73/53.01 |
| 5,297,420 | A * | 3/1994 | Gilliland | G01N 15/08 73/38 |
| 5,341,879 | A * | 8/1994 | Stone | E21B 43/04 166/278 |
| 5,847,268 | A * | 12/1998 | Ball | G01N 11/08 73/54.09 |
| 7,100,427 | B2 * | 9/2006 | Kahn | G01N 33/18 73/53.01 |
| 7,231,973 | B2 | 6/2007 | Sloan | |
| 7,377,169 | B2 | 5/2008 | Myers et al. | |
| 7,736,521 | B2 | 6/2010 | Sloan et al. | |
| 7,805,982 | B2 | 10/2010 | Hilab | |
| 7,832,257 | B2 * | 11/2010 | Weightman | E21B 43/26 73/54.09 |
| 8,122,759 | B2 * | 2/2012 | Weightman | E21B 43/26 73/54.09 |
| 8,383,560 | B2 | 2/2013 | Pich et al. | |
| 8,683,858 | B2 * | 4/2014 | Piri | C09K 8/58 73/152.05 |
| 8,714,247 | B1 | 5/2014 | Berger et al. | |
| 8,853,136 | B2 | 10/2014 | Bittner et al. | |
| 9,103,193 | B2 * | 8/2015 | Coli | E21B 43/26 |
| 2002/0011450 | A1 * | 1/2002 | Kelly | B01D 61/14 210/767 |
| 2006/0020427 | A1 * | 1/2006 | Kahn | G01N 33/1886 702/188 |
| 2009/0090504 | A1 * | 4/2009 | Weightman | E21B 43/26 166/250.01 |
| 2010/0000508 | A1 * | 1/2010 | Chandler | F24H 1/06 126/116 R |
| 2010/0083730 | A1 * | 4/2010 | Le | G01K 3/005 73/1.02 |
| 2010/0292110 | A1 * | 11/2010 | Pope | C08F 214/18 507/226 |
| 2012/0074069 | A1 * | 3/2012 | Ripley | B01D 35/1435 210/741 |
| 2012/0127466 | A1 * | 5/2012 | Karnes | G01N 11/04 356/319 |
| 2013/0104630 | A1 * | 5/2013 | Varni | G01N 11/08 73/54.09 |
| 2013/0191046 | A1 * | 7/2013 | Henning | G01N 11/04 702/50 |
| 2013/0298644 | A1 | 11/2013 | Dean et al. | |
| 2014/0116689 | A1 | 5/2014 | Bittner et al. | |
| 2014/0332473 | A1 * | 11/2014 | Haberman | C02F 1/004 210/741 |
| 2015/0168284 | A1 * | 6/2015 | Minton | G01N 11/08 73/54.09 |
| 2015/0343348 | A1 * | 12/2015 | Morris | G01L 13/00 210/90 |
| 2016/0122622 | A1 | 5/2016 | Dwarakanath et al. | |
| 2016/0122623 | A1 | 5/2016 | Dwarakanath et al. | |
| 2016/0122624 | A1 | 5/2016 | Dwarakanath et al. | |
| 2016/0122626 | A1 | 5/2016 | Dwarakanath et al. | |
| 2017/0284918 | A1 * | 10/2017 | Palazzo | G01N 11/04 |
| 2018/0010994 | A1 * | 1/2018 | Macomber | G01N 9/36 |
| 2018/0031462 | A1 | 2/2018 | Dwarakanath et al. | |

FOREIGN PATENT DOCUMENTS

| | | |
|---|---|---|
| WO | 2016/142623 A1 | 9/2016 |
| WO | 2017/046623 A1 | 3/2017 |

OTHER PUBLICATIONS

Schlumberger Oilfield Glossary entry for "capillary tube viscometer", accessed via www.glossary.oilfield.slb.com on Aug. 20, 2018.*
"FLOQUIP™ VDH—Inline Viscometer"; SNF Floerger, Production Bulletin, (Nov. 2013), 1 page.
Dwarakanath, Varadarajan, et al.; "Permeability Reduction Due to Use of Liquid Polymers and Development of Remediation Options"; SPE-179657-MS, Apr. 2016, pp. 1-18.
Koh, Heesong; "Experimental Investigation of the Effect of Polymers on Residual Oil Saturation"; Dissertation, The University of Texas at Austin, Jan. 2015, Title and Dedication pages, pp. v-xxv, and pp. 3-45.
Koh, Heesong; "Experimental Investigation of the Effect of Polymers on Residual Oil Saturation"; Dissertation, The University of Texas at Austin, Jan. 2015, pp. 46-116.
Koh, Heesong; "Experimental Investigation of the Effect of Polymers on Residual Oil Saturation"; Dissertation, The University of Texas at Austin, Jan. 2015, pp. 117-187.
Koh, Heesong; "Experimental Investigation of the Effect of Polymers on Residual Oil Saturation"; Dissertation, The University of Texas at Austin, Jan. 2015, pp. 188-257.
Levitt, David B., et al.; "The Effect of Redox Potential and Metal Solubility on Oxidative Polymer Degradation"; SPE 129890, Jun. 2011, pp. 287-298.
Levitt, David B.; "The Optimal Use of Enhanced Oil Recovery Polymers Under Hostile Conditions"; Dissertation, The University of Texas at Austin, May 2009, Title and Dedication pages pp. v-50.
Levitt, David B.; "The Optimal Use of Enhanced Oil Recovery Polymers Under Hostile Conditions"; Dissertation, The University of Texas at Austin, May 2009, pp. 51-116.
Levitt, David B.; "The Optimal Use of Enhanced Oil Recovery Polymers Under Hostile Conditions"; Dissertation, The University of Texas at Austin, May 2009, pp. 117-179, and Vita page.
Slaughter, Will Sherman; "Stability of Polymers Used for Enhanced Oil Recovery"; Thesis, The University of Texas at Austin, May 2010, Title and Dedication pages, pp. v-52.
Slaughter, Will Sherman; "Stability of Polymers Used for Enhanced Oil Recovery"; Thesis, The University of Texas at Austin, May 2010, pp. 53-125.
Slaughter, Will Sherman; "Stability of Polymers Used for Enhanced Oil Recovery"; Thesis, The University of Texas at Austin, May 2010, pp. 126-196.
Espinosa, David, et al.; "Dynamic Field Rheology, Filterability and Injectivity Characterization Using a Portable Measurement Unit"; SPE-190329-MS, pp. 12.
Magbagbeola, Oluwaseun Adedeji; "Quantification of the Viscoelastic Behavior of High Molecular Weight Polymers used for Chemical Enhanced Oil Recovery"; Thesis, Dec. 2008, pp. i-xx, pp. 1-48.
Magbagbeola, Oluwaseun Adedeji; "Quantification of the Viscoelastic Behavior of High Molecular Weight Polymers used for Chemical Enhanced Oil Recovery"; Thesis, Dec. 2008, pp. 49-117.

(56) References Cited

OTHER PUBLICATIONS

Magbagbeola, Oluwaseun Adedeji; "Quantification of the Viscoelastic Behavior of High Molecular Weight Polymers used for Chemical Enhanced Oil Recovery"; Thesis, Dec. 2008, pp. 118-185.

* cited by examiner

| LEGEND | |
|---|---|
| L01 | UPSTREAM PRESSURE |
| L02 | PROCESS INLET |
| L03 | PT ISOLATION |
| L04 | 110/120 SAND PACK FILTRATION |
| L05 | FILTRATION BYPASS |
| L06 | DOWNSTREAM PRESSURE |
| L07 | OUT FROM FILTRATION |
| L08 | PRV: SET PRESSURE 100 PSI |
| L09 | PRV: SET PRESSURE 50 PSI |
| L10 | IN FROM FILTRATION |
| L11 | OUT FROM PRESSURE VESSEL |
| L12 | VESSEL BYPASS |
| L13 | 200 PRESSURE VESSEL |
| L14 | DIFFERENTIAL PRESSURE |
| L15 | OUT TO FILTRATION RATIO |
| L16 | BLEED |
| L17 | DI WATER IN |
| L18 | DI WATER OUT |
| L19 | REGULATED GAS IN |
| L20 | REGULATED GAS PRESSURE |
| L21 | PRESSURE REDUCING REGULATOR |
| L22 | COMPRESSED GAS INLET |
| L23 | SYRINGE PUMP |
| L24 | TO VESSEL PROCESS SIDE |
| L25 | 150/155 CAPILLARY VISCOMETER |
| L26 | IN FROM PRESSURE VESSEL |
| L27 | CORE INLET TEMPERATURE |
| L28 | 170 CORE |
| L29 | CORE IN |
| L30 | CORE TAP |
| L31 | CORE TAP OUT |
| L32 | BLEED FOR CORE INLET |
| L33 | CORE OUT |
| L34 | CORE INLET PRESSURE |
| L35 | CORE OUTLET TEMPERATURE |
| L36 | CORE OUTLET PRESSURE |
| L37 | BACK PRESSURE REGULATOR |
| L38 | VENT |
| L39 | OUTLET |
| L40 | BYPASS |
| L41 | OXIDATION REDUCTION POTENTIAL MEASUREMENT |

FIG. 4 Continued

PORTABLE APPARATUS AND METHODS FOR ANALYZING INJECTION FLUIDS

CROSS REFERENCES TO RELATED APPLICATIONS

This application claims the benefit of U.S. Provisional Application No. 62/367,567, filed Jul. 27, 2016, and U.S. Provisional Application No. 62/431,352, filed Dec. 7, 2016, the disclosures of which are expressly incorporated herein by reference. This application is a continuation of, and claims the benefit to, U.S. Non-provisional application Ser. No. 15/661,914, filed Jul. 27, 2017, the disclosure of which is incorporated by reference.

TECHNICAL FIELD

The present disclosure is generally related to systems and methods for the analysis of an injection fluid used in an oil and gas operation, such as in an enhanced oil recovery application.

BACKGROUND

A fluid is sometimes injected into a hydrocarbon-formation to improve hydrocarbon production. For example, one conventional method of enhanced oil recovery (EOR) includes the injection of a fluid containing a polymer into a formation. A formation can be flooded with polymer to control (e.g., decrease) the mobility of water that is injected into the formation during a waterflood, reduce the permeability of the formation, and/or to increase sweep efficiency. The polymer can be used either alone or in combination with at least one other component, such as a surfactant. A polymer flood, as it is often called, can increase the rate and/or total volume of produced hydrocarbon and can be used as an alternative to thermal EOR methods, for example, in the production of heavy or viscous oil.

In a typical polymer flood, polymer from a source is mixed on-site with a fluid to form an injection fluid and then the injection fluid is injected into the formation through the well head equipment of one or more wells. The mixing process can vary depending on the initial state of the polymer as it is supplied. Unfortunately, it is sometimes difficult to deliver the injection fluid containing the polymer into the formation. For example, the injection fluid containing the polymer may sometimes obstruct or plug up some of the equipment, the formation, or both, which inhibits proper flow of the injection fluid into the formation. As an example, incorrect mixing of the polymer into the fluid, incomplete hydration of powder polymer, incorrect mixing ratios, or any combination of these may cause the plugging. Even fluids without polymers may sometimes cause plugging.

In short, many injection fluids sometimes cause plugging, and understanding and controlling the characteristics of injection fluids can be a significant factor in any flood to produce hydrocarbons. One such characteristic is the viscosity of the injection fluid. The viscosity can be measured before the injection fluid is injected into the formation. One method of measuring viscosity includes using an in-line viscometer that operates in real-time, for example, as described in US Patent Application Publication 2013/0298644, which is incorporated herein by reference in its entirety.

However, simply knowing the viscosity alone generally does not provide enough information about an injection fluid to avoid plugging. According to Dwarakanath et al., "Permeability reduction due to use of liquid polymers and development of remediation options," Society of Petroleum Engineers, SPE-179657-MS, Apr. 11-13, 2016, pages 1-18, which is incorporated herein by reference in its entirety, characteristics such as long term injectivity and filter ratio may be helpful in getting a better understanding of injection fluids. However, conventional portable devices typically do not measure long term injectivity or filter ratio, and if any of these tests are performed, they typically require a laboratory setting, which leads to degradation of injection fluid samples, delays, etc.

Therefore, a need exists in the art for a better way to analyze injection fluids, especially analysis around long term injectivity and filter ratio, and especially in non-laboratory settings, such as offshore facility, remote well sites, etc.

SUMMARY

Provided herein are portable apparatus for analyzing injection fluids. The portable apparatus can comprise a housing encompassing one or more components of the portable apparatus. The components of the portable apparatus can comprise an inlet to receive the injection fluid; a pre-filter coupled to the inlet; a pump coupled to the pre-filter to direct the injection fluid from the pre-filter through one or more analytical modules chosen from a surrogate core, a capillary viscometer, a filter, or a combination thereof; one or more pressure transducers chosen from a pressure transducer coupled to the pre-filter, a pressure transducer coupled to any of the one or more analytical modules, or a combination thereof; a data acquisition system (DAS) that receives data from the one or more pressure transducers and calculates a property of the injection fluid from the data; and a power supply coupled to the pump, the one or more pressure transducers, and the data acquisition system to provide power. Depending upon the identity of the one or more analytical modules included in the apparatus, the can be used to determine the long term injectivity of the injection fluid, the viscosity of the injection fluid, the filter ratio of the injection fluid, or any combination thereof.

In some embodiments, the components of the portable apparatus can comprise two or more analytical modules chosen from a surrogate core, a capillary viscometer, a filter, or a combination thereof. In these embodiments, the pump can be coupled to the pre-filter to direct the injection fluid from the pre-filter through the two or more analytical modules.

In certain embodiments, the components of the portable apparatus comprise three analytical modules. The three analytical modules comprise a surrogate core, a capillary viscometer, and a filter. In these embodiments, the pump can be coupled to the pre-filter to direct the injection fluid from the pre-filter through the three analytical modules. In certain of these embodiments, the one or more pressure transducers can comprise a pressure transducer coupled to the pre-filter to measure a differential pressure of the injection fluid across the pre-filter, a pressure transducer coupled to the surrogate core to measure a differential pressure of the injection fluid across the surrogate core, a pressure transducer coupled to the capillary viscometer to measure a differential pressure of the injection fluid across the capillary viscometer, and a pressure transducer coupled to the filter to measure an absolute pressure of the injection fluid to be filtered through the filter. In these embodiments, the apparatus can be used to simultaneously determine the long term injectivity, viscosity, and filter ratio of an injection fluid.

In some cases, the apparatus can further comprise a pressure vessel coupled to the pre-filter to receive and store injection fluid from the pre-filter. The pressure vessel can further be coupled to the one or more analytical modules to deliver the injection fluid from the pressure vessel to the one or more analytical modules. The pump can be coupled to the pressure vessel to pump the injection fluid through the pressure vessel. In some cases, a gas line can be coupled to the pressure vessel to actuate the pressure vessel.

If desired for a particular application, the apparatus can further comprise additional analytical modules, such as a temperature probe, a pH probe, a conductivity probe, an oxidation reduction potential probe, or a combination thereof.

Also provided herein are methods of analyzing injection fluids using the apparatus described herein. If desired, the portable nature of the apparatus allows the apparatus to be used to analyze an injection fluid onsite at or near an injection well. Further, the apparatus can be used to perform continuous and/or real-time measurements of properties of injection fluids, including the long term injectivity, viscosity, and filter ratio of an injection fluid. This information can be used to monitor the characteristics of an injection fluid over time, allowing technicians to rapidly correct any deficiencies in the as-prepared injection fluid as compared to a specified target composition. This can be implemented, for example, as part of a quality assurance program associated with an oil and gas operation, such as hydrocarbon recovery.

Accordingly, also provided or methods for hydrocarbon recovery that employ the apparatus described herein to measure and/or monitor the properties of an injection fluid utilized during the hydrocarbon recovery process. These methods for hydrocarbon recovery can comprise (a) providing a subsurface reservoir containing hydrocarbons there within; (b) providing a wellbore in fluid communication with the subsurface reservoir; (c) mixing an injection fluid and flowing the injection fluid through a fluid conduit to the wellbore; (d) measuring a property of the injection fluid flowing through the fluid conduit using a portable apparatus described herein; and (e) injecting the injection fluid through the wellbore into the subsurface reservoir. The inlet of the portable apparatus can be fluidly connected to the fluid conduit, thereby forming a closed path for fluid flow from the fluid conduit to the one or more analytical modules in the portable apparatus. This ensures that the fluid remains in a reduced environment until after is has been processed by the analytical modules. As a consequence, the properties measured by the analytical modules can accurately reflect the properties of the injection fluid upon injection into an injection well.

In some embodiments, the method can further comprise (f) comparing the property of the injection fluid measured in step (d) with a target value or range; and (g) altering the mixing of the injection fluid in step (c) to improve correlation between the property of the injection fluid measured in step (d) and the target value or range. By way of example, in certain embodiments, step (d) can comprise measuring a filter ratio of the injection fluid flowing through the fluid conduit using a portable apparatus in which the one or more analytical modules comprises a 1.2 micron filter having a diameter of 47 mm or 90 mm. In these embodiments, step (f) can comprise comparing the filter ratio of the injection fluid measured in step (d) the target value or range of 1.5 or less, and step (f) can comprise altering the mixing of the injection fluid in step (c) to reduce the filter ratio of the injection fluid to a value of 1.5 or less. Altering the mixing of the injection fluid in step (f) can comprise, for example, changing feedstock mixed to form the injection fluid, varying ratios of feedstock mixed to form the injection fluid, changing a mixer used to mix the injection fluid, or a combination thereof. In some embodiments, steps (d), (f), and optionally (g) are performed continuously.

DESCRIPTION OF THE DRAWINGS

The figures are provided that illustrate various embodiments of portable systems and methods of determining viscosity, long term injectivity, filter ratio, or any combination thereof of an injection fluid. In some embodiments, the injection fluid contains a polymer, but a polymer is not necessary. The scope of the claims is not limited to the embodiments and figures provided with this disclosure.

DETAILED DESCRIPTION

Definitions

Figure 1:
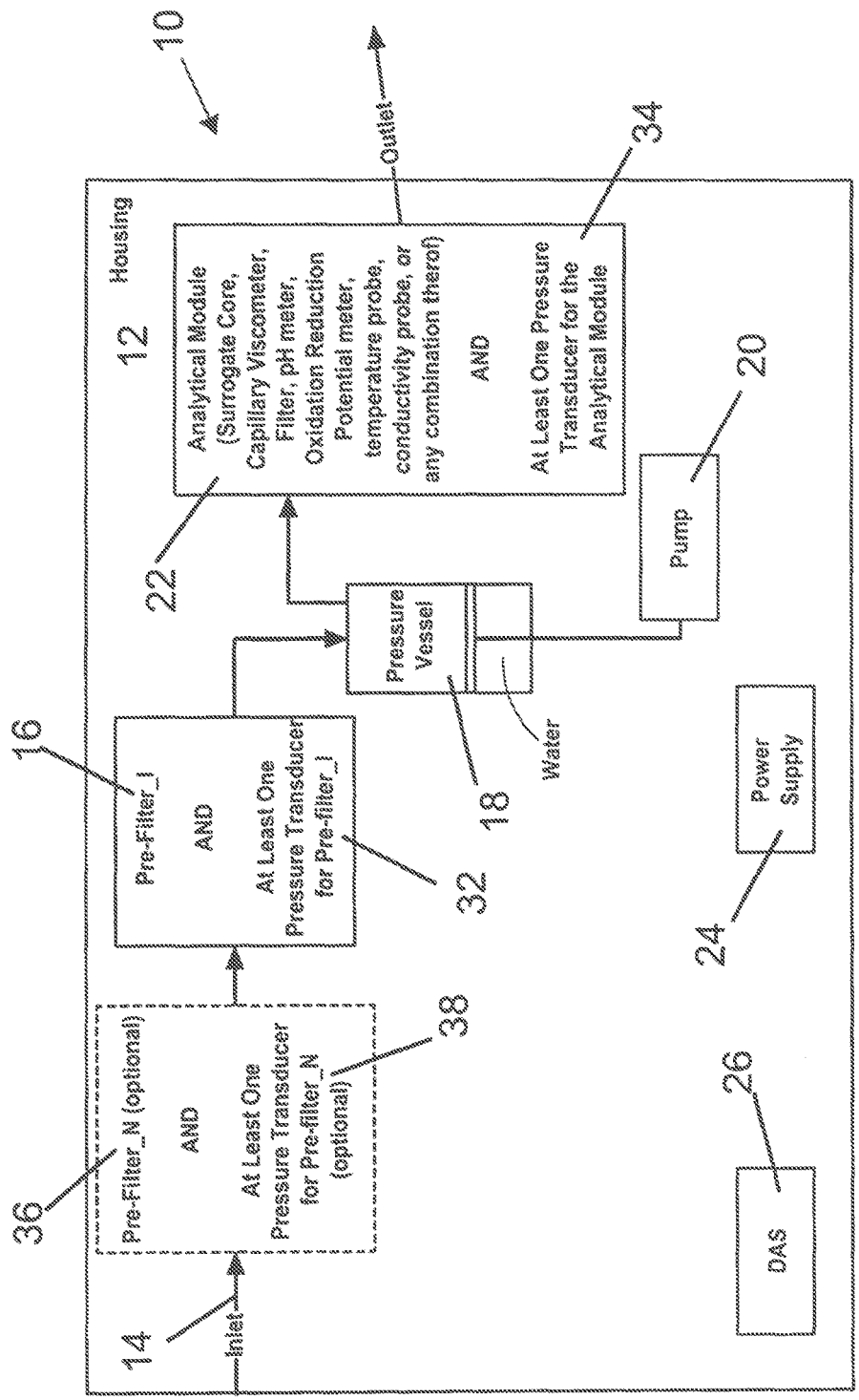
FIG. 1 is a schematic illustration of the components of a portable apparatus for analyzing an injection fluid.

The following terms will be used throughout the specification and will have the following meanings unless otherwise indicated.

Hydrocarbon: The terms "hydrocarbon" or "hydrocarbonaceous" or "petroleum" or "crudes" or "oil" (and variants) may be used interchangeably to refer to carbonaceous material originating from subterranean formations as well as synthetic hydrocarbon products, including organic liquids or gases, kerogen, bitumen, crude oil, natural gas or from biological processes, that is principally hydrogen and carbon, with significantly smaller amounts (if any) of heteroatoms such as nitrogen, oxygen and sulfur, and, in some cases, also containing small amounts of metals. Crude oil (e.g., liquid petroleum) and natural gas (e.g., gaseous petroleum) are both hydrocarbons.

Hydrocarbon-bearing formation: The terms "hydrocarbon-bearing formation" or "formation" may be used interchangeably and refer to the hydrocarbon bearing reservoir rock matrix in which at least one wellbore (e.g., an injection wellbore) is present. For example, a formation refers to a body of hydrocarbon bearing reservoir rock that is sufficiently distinctive and continuous such that it can be mapped. It should be appreciated that while the term "formation" generally refers to geologic formations of interest, that the term "formation," as used herein, may, in some instances, include any reservoirs, geologic points, or volumes of interest (such as a survey area). The term formation is not limited to any structure and configuration described herein. The term formation may be used synonymously with the term reservoir.

Wellbore: The term "wellbore" refers to a single hole drilled into the formation for use in hydrocarbon recovery. The wellbore can be used for injection, production, or both. The wellbore may include casing, liner, tubing, other items, or any combination thereof. Casing is typically cemented into the wellbore with the cement placed in the annulus between the formation and the outside of the casing. Tubing and liners are typically not cemented in the wellbore. The wellbore may include an openhole portion or uncased portion. The wellbore is surrounded by the formation. The wellbore may be vertical, inclined, horizontal, or combination trajectories. The wellbore may include any completion hardware that is not discussed separately. The term wellbore is not limited to any structure and configuration described herein. The term wellbore may be used synonymously with the terms borehole or well. For simplicity, a "production wellbore" enables the removal of fluids from the formation to the surface and an "injection wellbore" enables the placement of fluid into the formation from the surface.

Enhanced oil recovery: The term "enhanced oil recovery" refers to techniques for increasing the amount of hydrocarbons (e.g., oil, gas, a mixture of oil and gas, etc.) that may be extracted from a hydrocarbon-bearing formation. Enhanced oil recovery may also be referred to as improved oil recovery or tertiary oil recovery (as opposed to primary and secondary oil recovery). Regardless of the alternative terminology, examples of EOR include, for example, (a) miscible gas injection (which includes, for example, carbon dioxide flooding), (b) chemical injection (sometimes referred to as chemical enhanced oil recovery (CEOR), and which includes, for example, polymer flooding, alkaline flooding, surfactant flooding, conformance control operations, as well any combination thereof such as alkaline-polymer flooding, surfactant-polymer flooding, or alkaline-surfactant-polymer flooding), (c) microbial injection, (d) thermal recovery (which includes, for example, cyclic steam, steam flooding, and fire flooding), and (e) co-solvent-alkaline polymer flooding. In some embodiments, the EOR operation can include a polymer (P) flooding operation, an alkaline-polymer (AP) flooding operation, a surfactant-polymer (SP) flooding operation, an alkaline-surfactant-polymer (ASP) flooding operation, a conformance control operation, or any combination thereof. The terms "operation" or "application" or "treatment" may be used interchangeability herein, as in an EOR operation or an EOR application or an EOR treatment.

Injection fluid/Brine: The term "injection fluid" refers to a fluid that will be injected into a formation, for example, via a wellbore, such as an injection wellbore. The injection fluid may include a brine or aqueous phase, but it may also include gas, such as a mixture of brine and gas. The brine may be practically any liquid that may be injected into a hydrocarbon-bearing formation. The brine may be surface water, water recovered from a production wellbore, sea water, produced formation brine, formation brine, fresh water, produced water, water, saltwater, synthetic brine, synthetic seawater brine, or any combination thereof. In some embodiments, brines may include, but are not necessarily limited to, heavy brines, monovalent brines, divalent brines, and trivalent brines that comprise soluble salts like sodium chloride, calcium chloride, calcium bromide, zinc bromide, potassium carbonate, sodium formate, potassium formate, cesium formate, sodium acetate, potassium acetate, calcium acetate, ammonium acetate, ammonium chloride, ammonium bromide, sodium nitrate, potassium nitrate, ammonium nitrate, ammonium sulfate, calcium nitrate, sodium carbonate, potassium carbonate, any derivative thereof, or any combination thereof.

The injection fluid may include at least one polymer, which may be practically any polymer that may be injected into a hydrocarbon-bearing formation. The injection fluid can be mixed on-site to include the polymer, e.g., by mixing the polymer in the form of a powder, gel, emulsion, or liquid, with a solute such as water. Depending on the specific embodiment, the "polymer" may be a polymer composition, a polymer solution, a polymer suspension, polymer dispersion, a liquid polymer, etc. In short, the "polymer" itself may be made up of various constituents. In some embodiments, the polymer can be a component of the injection fluid. Besides the polymer and the brine of the injection fluid, the injection fluid may include at least one other component (e.g., at least one solvent, at least one optional additive, etc.) in some embodiments. This other component may also be a constituent of the polymer, for example, a solvent in the form of a surfactant may be a constituent of the polymer. The other component may also be mixed on-site.

Of note, the injection fluid may not contain a polymer in some embodiments. Indeed, the injection fluid may contain a surfactant only in one embodiment; produced water only in a second embodiment; an alkali only in a third embodiment; so on.

Polymer: The term "polymer" refers to practically any polymer that may be injected into a hydrocarbon-bearing formation. For example, the polymer can be initially provided as a powder that is mixed on-site, or the polymer can be initially provided in a partial-strength solution, such as gel, emulsion, or other fluid that is made up partly of polymer (e.g., 2%-60% polymer) in a solute such as water or a brine as discussed hereinabove. As discussed herein, the injection fluid can be mixed on-site to include the polymer, e.g., by mixing the polymer in the form of a powder, gel, emulsion, or liquid, with a solute such as water.

Regarding the polymer, a powder polymer may be selected or tailored according to the characteristics of the formation for EOR treatment such as permeability, temperature, and salinity. Examples of suitable powder polymers include biopolymers such as polysaccharides. For example, polysaccharides can be xanthan gum, scleroglucan, guar gum, schizophyllan, any derivative thereof (e.g., such as a modified chain), or any combination thereof. Indeed, the terminology "mixtures thereof" or "combinations thereof" can include "modifications thereof" herein. Examples of suitable powder synthetic polymers include polyacrylamides. Examples of suitable powder polymers include synthetic polymers such as partially hydrolyzed polyacrylamides (HPAMs or PHPAs) and hydrophobically-modified associative polymers (APs). Also included are co-polymers of polyacrylamide (PAM) and one or both of 2-acrylamido 2-methylpropane sulfonic acid (and/or sodium salt) commonly referred to as AMPS (also more generally known as acrylamido tertiobutyl sulfonic acid or ATBS), N-vinyl pyrrolidone (NVP), and the NVP-based synthetic may be single-, co-, or ter-polymers. In one embodiment, the powder synthetic polymer comprises polyacrylic acid (PAA). In one embodiment, the powder synthetic polymer comprises polyvinyl alcohol (PVA). Copolymers may be made of any combination or mixture above, for example, a combination of NVP and ATBS. Thus, examples of suitable powder polymers include biopolymers or synthetic polymers. Examples of suitable powder polymers can also include any mixture of these powder polymers (including any modifications of these powder polymers).

In one embodiment, the powder polymer is an anionic polyacrylamide having a charge ranging from 0 to about 40%, which may be resultant because the reaction to form polyacrylamide generally starts with about 0% to about 40% acrylic acid or acid salt. The polymer that may be formed with acrylic acid or an acid salt monomer is called anionic polyacrylamide because the polymer itself contains a negative charge, which is balanced by a cation, usually sodium. A polymer made with little or no acid or acid salt is considered nonionic polyacrylamide because the polymer essentially contains no charge. The powder polymer has an average molecular weights (Mw) of: 0.5 to 30 Million Daltons in one embodiment; from 1 to 15 Million Daltons in a second embodiment; at least 2 Million Daltons in a third embodiment; from 4 to 25 Million Daltons in a fourth embodiment; less than or equal to 25 Million Daltons in a fifth embodiment; and at least 0.5 Million Daltons in a sixth embodiment.

The polymer powders have an average particle size of at least 5 mesh in one embodiment, 10-100 mesh in a second embodiment, and 40-400 mesh in a third embodiment. The polymer powder undergoes an additional milling, grinding, or crushing prior to mixing with the water soluble solvent in the preparation, for a particle size of 1-1000 μm in one embodiment; from 10-500 μm in a second embodiment; at least 5 μm in a third embodiment; and from 20-500 μm in a fourth embodiment.

Solvent: The term "solvent" may refer to practically any solvent that may be injected into a hydrocarbon-bearing formation. The solvent may be a water soluble solvent. The water soluble solvent may be selected from one or more of surfactants (e.g., non-ionic surfactants), ethers (e.g., glycol ethers), alcohols, co-solvents, or any combination thereof, for an HLB of greater than or equal to 8 (e.g., at least 8) as measured by methods known in the art, e.g., NMR, gas-liquid chromatography, or invert emulsion experiments using Griffin's method or Davies's method. In one embodiment, the HLB is about 10.0 to about 20. In another embodiment, the HLB is less than or equal to 15. Examples of suitable water soluble solvents can also include any mixture of these water soluble solvents (including any modifications of these water soluble solvents). For example, the water soluble solvent can include a mixture of non-ionic and anionic surfactants. The anionic surfactant can be present in an amount of less than or equal to 5 wt. % as a stabilizer.

Examples of suitable water soluble solvents include but are not limited to alcohol ethoxylates (-EO-), alcohol alkoxylates (-PO-EO-), alkyl polyglycol ethers, alkyl phenoxy ethoxylates, an ethylene glycol butyl ether (EGBE), a diethylene glycol butyl ether (DGBE); a triethylene glycol butyl ether (TGBE), polyoxyethylene nonylphenylether, branched, or any combination thereof. In one embodiment, the water soluble solvent comprises an alcohol, such as isopropyl alcohol (IPA), isobutyl alcohol (IBA), secondary butyl alcohol (SBA), or any combination thereof. In another embodiment, the water soluble solvent comprises a low MW ether such as ethylene glycol monobutyl ether.

In embodiments with the use of HPAM type synthetic polymers, a non-ionic surfactant is used as the water soluble solvent. In yet another embodiment, a mixture or combination of surfactants is used, e.g., non-ionic surfactants and anionic surfactants in a weight ratio ranging from 6:1 to 2:1. Examples of non-ionic surfactants for use as the water soluble solvents comprise ethoxylated surfactants, nonylphenol ethoxylates or alcohol ethoxylate, other ethoxylated surfactants, or any combination thereof. In another embodiment, the anionic surfactants comprise internal olefin sulfonates, isomerized olefin sulfonates, alkyl aryl sulfonates, medium alcohol (C10 to C17) alkoxy sulfates, alcohol ether [alkoxy]carboxylates, alcohol ether [alkoxy]sulfates, alkyl sulfonate, α-olefin sulfonates (AOS), dihexyl sulfosuccinate, or any combination thereof. In yet another embodiment, the water soluble solvent comprises alkylpolyalkoxy sulfates as disclosed in U.S. Pat. No. 8,853,136, sulfonated amphoteric surfactants as disclosed in U.S. Pat. No. 8,714,247, surfactants based on anionic alkyl alkoxylates as disclosed in US Patent Publication No. 20140116689, or any combination thereof, each of which are incorporated herein by reference in its entirety.

In one embodiment, the water soluble solvent comprises isopropyl alcohol (IPA), n-propyl alcohol, isobutyl alcohol (IBA), methyl-isobutyl alcohol, secondary butyl alcohol (SBA), ethylene glycol monobutyl ether, diethylene glycol monobutyl ether, triethylene glycol monobutyl ether, or any combination thereof. In one embodiment, the water soluble solvent comprises an ionic surfactant selected from ethoxylated surfactants, nonylphenol ethoxylates, alcohol ethoxylates, internal olefin sulfonates, isomerized olefin sulfonates, alkyl aryl sulfonates, medium alcohol (C10 to C17) alkoxy sulfates, alcohol ether [alkoxy]carboxylates, alcohol ether [alkoxy]sulfates, alkyl sulfonate, α-olefin sulfonates (AOS), dihexyl sulfosuccinates, alkylpolyalkoxy sulfates, sulfonated amphoteric surfactants, or any combination thereof. Examples of suitable water soluble solvents can also include any combination or mixture of these water soluble solvents (including any modifications of these water soluble solvents).

In one embodiment, the water soluble solvent comprises a co-solvent, and the co-solvent comprises ionic surfactant, non-ionic surfactant, anionic surfactant, cationic surfactant, nonionic surfactant, amphoteric surfactant, ketones, esters, ethers, glycol ethers, glycol ether esters, lactams, cyclic ureas, alcohols, aromatic hydrocarbons, aliphatic hydrocarbons, alicyclic hydrocarbons, nitroalkanes, unsaturated hydrocarbons, halocarbons, surfactants commonly used for enhanced oil recovery applications, alkyl aryl sulfonates (AAS), a-olefin sulfonates (AOS), internal olefin sulfonates (IOS), alcohol ether sulfates derived from propoxylated $Ci_2$-$C_2$o alcohols, ethoxylated alcohols, mixtures of an alcohol and an ethoxylated alcohol, mixtures of anionic and cationic surfactants, disulfonated surfactants, aromatic ether polysulfonates, isomerized olefin sulfonates, alkyl aryl sulfonates, medium alcohol (C10 to C17) alkoxy sulfates, alcohol ether [alkoxy]carboxylates, alcohol ether [alkoxy] sulfates, primary amines, secondary amines, tertiary amines, quaternary ammonium cations, cationic surfactants that are linked to a terminal sulfonate or carboxylate group, alkyl aryl alkoxy alcohols, alkyl alkoxy alcohols, alkyl alkoxylated esters, alkyl polyglycosides, alkoxy ethoxyethanol compounds, isobutoxy ethoxyethanol ("iBDGE"), n-pentoxy ethoxyethanol ("n-PDGE"), 2-methylbutoxy ethoxyethanol ("2-MBDGE"), methylbutoxy ethoxyethanol ("3-MBDGE"), (3,3-dimethylbutoxy ethoxyethanol ("3,3-DMBDGE"), cyclohexylmethyleneoxy ethoxyethanol (hereafter "CHMDGE"), 4-Methylpent-2-oxy ethoxyethanol ("MIBCDGE"), n-hexoxy ethoxyethanol (hereafter "n-HDGE"), 4-methylpentoxy ethoxyethanol ("4-MP-DGE"), butoxy ethanol, propoxy ethanol, hexoxy ethanol, isoproproxy 2-propanol, butoxy 2-propanol, propoxy 2-propanol, tertiary butoxy 2-propanol, ethoxy ethanol, butoxy ethoxy ethanol, propoxy ethoxy ethanol, hexoxy ethoxy ethanol, methoxy ethanol, methoxy 2-propanol and ethoxy ethanol, n-methyl-2-pyrrolidone, dimethyl ethylene urea, or any combination thereof. Examples of suitable co-solvents can also include any mixture of these co-solvents (including any modifications of these co-solvents)

The term "optional additive" refers to practically any other additive that may be injected into the formation. Examples of optional additives comprise anionic surfactants, biocides, co-solvents, chelators, reducing agents/oxygen scavengers, stabilizers, etc., or any combination thereof, in an amount of less than or equal to 10 wt. % (of the total weight of the polymer suspension). In one embodiment, a stabilizer is added to further stabilize the suspended polymer. For example, an anionic surfactant can be present in an amount of less than or equal to 5 wt. % as a stabilizer.

Some polymers, solvents, and/or optional additives that may be used herein are discussed in more detailed in the following cases having Chevron U.S.A. Inc. as an assignee: US Patent Application Publication Nos. 2016/0122622, 2016/0122626, 2016/0122623, and 2016/0122624, each of which is incorporated herein by reference in its entirety. More information may also be found in Dwarakanath et al., "Permeability Reduction Due to use of Liquid Polymers and Development of Remediation Options," SPE 179657, SPE IOR Symposium in Tulsa, 2016, which is incorporated herein by reference in its entirety.

Viscosity: The term "viscosity" refers to thickness of the injection fluid.

Long term injectivity: The term "long term injectivity" refers to the change in pressure, if any, over a time period that includes many pore volumes of fluid injection at a constant temperature, constant injection rate, and constant viscosity. A constant pressure, with little change, indicates favorable long term injectivity. An increase in pressure over the time period indicates unfavorable long term injectivity. In some embodiments, the number of pore volumes of fluid injection is at least 20. In some embodiments, the number of pore volumes of fluid injection is at least 30. In some embodiments, the number of pore volumes of fluid injection is at least 50. In some embodiments, the number of pore volumes of fluid injection is at least 100. In some embodiments, the number of pore volumes of fluid injection is at least 200. In some embodiments, the number of pore volumes of fluid injection is at least 500. In some embodiments, the number of pore volumes of fluid injection is at least 1000. In some embodiments, the number of pore volumes of fluid injection is in a range of about 20 pore volumes and 100 pore volumes. In some embodiments, the number of pore volumes of fluid injection is in a range of about 100 pore volumes and 500 pore volumes.

Filterability/FR: The term "filterability" refers to the mobility control property of an injection fluid, or the ability to move unimpeded through the formation without blocking the pores of the formation. "Filter ratio" (or filterability ratio) test is a recognized laboratory test to measure the ability of an aqueous flooding fluid, such as the injection fluid, to move through the formation without blocking the pores of the formation, as described in The American Petroleum Institute standards RP 63. Ideally, an aqueous flooding fluid should pass through the filter at a constant rate throughout the test, causing no pore-blocking during filtration, with a filter ratio=1.0. The actual measured filter ratio is typically >1.0, however, so an upper limit to the filter ratio under a specific set of conditions is normally used in order to determine the suitability of an aqueous flooding fluid for use in a mobility control application.

For certain applications, including many enhanced oil recovery (EOR) applications, it can be desirable that the injection fluid flows through a hydrocarbon-bearing formation without plugging the equipment and without plugging the formation. Plugging the equipment, the formation, or both can make it difficult to injection the injection fluid into the formation. Furthermore, plugging the equipment, the formation, or both can slow or inhibit hydrocarbon production. This is an especially large concern in the case of hydrocarbon-bearing formations that have a relatively low permeability before enhanced oil recovery techniques are applied.

For purposes of this disclosure, including the claims, the filter ratio (FR) can be determined using a 1.2 micron filter at 15 psi (plus or minus 10% of 15 psi) at ambient temperature (e.g., 25° C.). The 1.2 micron filter can have a diameter of 47 mm or 90 mm, and the filter ratio can be calculated as the ratio of the time for 180 to 200 ml of the injection fluid to filter divided by the time for 60 to 80 ml of the injection fluid to filter:

$$FR = \frac{t200\ ml - t180\ ml}{t80\ ml - t60\ ml}$$

For purposes of this disclosure, including the claims, the apparatus disclosed herein will determine if the injection fluid exhibits a FR of 1.5 or less via the modified filter ratio test method described herein.

Of note: One test commonly used to determine performance involves measuring the time taken for given volumes/concentrations of solution to flow through a filter, commonly called a filtration quotient or Filter Ratio ("FR"). For example, U.S. Pat. No. 8,383,560 describes a filter ratio test method which measures the time taken by given volumes of a solution containing 1000 ppm of active polymer to flow through a filter. The solution is contained in a cell pressurized to 2 bars and the filter has a diameter of 47 mm and a pore size of 5 microns. The times required to obtain 100 ml (t100 ml), 200 ml (t200 ml), and 300 ml (t300 ml) of filtrate were measured. These values were used to calculate the FR, expressed by the formula below:

$$FR = \frac{t300\ ml - t200\ ml}{t200\ ml - t100\ ml}$$

The FR generally represents the capacity of the injected fluid to plug the filter for two equivalent consecutive volumes. Generally, a lower FR indicates better performance. U.S. Pat. No. 8,383,560, which is incorporated herein by reference, explains that a desirable FR using this method is less than 1.5. Filter ratio (FR) can also be determined using the standard procedure described, for example, in Koh, H. *Experimental Investigation of the Effect of Polymers on Residual Oil Saturation*. Ph.D. Dissertation, University of Texas at Austin, 2015; Levitt, D. *The Optimal Use of Enhanced Oil Recovery Polymers Under Hostile Conditions*. Ph.D. Dissertation, University of Texas at Austin, 2009; and Magbagbeola, O. A. Quantification of the Viscoelastic Behavior of High Molecular Weight Polymers used for Chemical Enhanced Oil Recovery. M.S. Thesis, University of Texas at Austin, 2008, each of which is hereby incorporated by reference in its entirety.

However, injection fluids containing polymers that provide desirable results using the test method of U.S. Pat. No. 8,383,560 have not necessarily provided acceptable performance in the field. In particular, many polymers that have an FR (using a 5 micron filter) lower than 1.5 exhibit poor injectivity—i.e., when injected into a formation, they tend to plug the formation, slowing or inhibiting oil production. A modified filter ratio test method using a smaller pore size (i.e., the same filter ratio test method except that the filter above is replaced with a filter having a diameter of 47 mm (or 90 mm) and a pore size of 1.2 microns) and lower pressure (15 psi) provides a better screening method. Injection fluids that satisfy a FR using the 1.2 micron filter of 1.5 or less are desirable, and in field testing, they may exhibit improved injectivity over other injection fluids having a FR (using a 5 micron filter) of less than 1.5. As such, the systems and methods described herein are suitable for applying this modified filter ratio test for use in a variety of oil and gas applications, including EOR.

Pore volume: "Pore volume" or "PV" fraction as used herein refers to the total volume of pore space in the formation that is contemplated in a sweep (e.g., contacted pore space at alkali-surfactant-polymer (ASP), surfactant-polymer (SP), alkali-polymer (AP), and/or polymer drive (PD) mobility ratio).

Pore throat: "Pore throat" refers to openings in sand/rock formation. Pore throat size in formation forms a continuum from the sub-millimeter to the nanometer scale. For measures of central tendency (mean, mode, median), pore throat sizes (diameters) are generally greater than 2 µm in conventional reservoir rocks, from about 2 to 0.03 µm in tight-gas sandstones, and from 0.1 to 0.005 µm in shales.

"Equal" refers to equal values or values within the standard of error of measuring such values. "Substantially equal" refers to an amount that is within 3% of the value recited.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention, inclusive of the stated value and has the meaning including the degree of error associated with measurement of the particular quantity. This term "about" generally refers to a range of numbers that one of ordinary skill in the art would consider as a reasonable amount of deviation to the recited numeric values (i.e., having the equivalent function or result). For example, this term "about" can be construed as including a deviation of ±10 percent of the given numeric value provided such a deviation does not alter the end function or result of the value. Therefore, a value of about 1% can be construed to be a range from 0.9% to 1.1%.

As used in this specification and the following claims, the terms "comprise" (as well as forms, derivatives, or variations thereof, such as "comprising" and "comprises") and "include" (as well as forms, derivatives, or variations thereof, such as "including" and "includes") are inclusive (i.e., open-ended) and do not exclude additional elements or steps. Other variants of "comprise" may be "have" and "contain" and the like. For example, the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Accordingly, these terms are intended to not only cover the recited element(s) or step(s), but may also include other elements or steps not expressly recited.

While various embodiments are described in terms of "comprising," "containing," or "including" various components or steps, the compositions and methods can also "consist essentially of" or "consist of" the various components and steps. "Consisting of" is closed, and excludes all additional elements. "Consisting essentially of" excludes additional material elements, but allows the inclusions of non-material elements that do not substantially change the nature of the invention.

Furthermore, as used herein, the use of the terms "a" or "an" when used in conjunction with an element may mean "one," but it is also consistent with the meaning of "one or more," "at least one," and "one or more than one." Thus, it is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the use of "may" or "may be" indicates that a modified term is appropriate, capable, or suitable for an indicated capacity, function, or usage, while taking into account that in some circumstances the modified term may sometimes not be appropriate, capable, or suitable. Furthermore, unless explicitly dictated by the language, the term "and" may be interpreted as "or" in some instances.

It is understood that when combinations, subsets, groups, etc. of elements are disclosed (e.g., combinations of components in an item, or combinations of steps in a method), that while specific reference of each of the various individual and collective combinations and permutations of these elements may not be explicitly disclosed, each is specifically contemplated and described herein. By way of example, if an item is described herein as including a component of type A, a component of type B, a component of type C, or any combination thereof, it is understood that this phrase describes all of the various individual and collective combinations and permutations of these components. For example, in some embodiments, the item described by this phrase could include only a component of type A. In some embodiments, the item described by this phrase could include only a component of type B. In some embodiments, the item described by this phrase could include only a component of type C. In some embodiments, the item described by this phrase could include a component of type A and a component of type B. In some embodiments, the item described by this phrase could include a component of type A and a component of type C. In some embodiments, the item described by this phrase could include a component of type B and a component of type C. In some embodiments, the item described by this phrase could include a component of type A, a component of type B, and a component of type C. In some embodiments, the item described by this phrase could include two or more components of type A (e.g., A1 and A2). In some embodiments, the item described by this phrase could include two or more components of type B (e.g., B1 and B2). In some embodiments, the item described by this phrase could include two or more components of type C (e.g., C1 and C2). In some embodiments, the item described by this phrase could include two or more of a first component (e.g., two or more components of type A (A1 and A2)), optionally one or more of a second component (e.g., optionally one or more components of type B), and optionally one or more of a third component (e.g., optionally one or more components of type C). In some embodiments, the item described by this phrase could include two or more of a first component (e.g., two or more components of type B (B1 and B2)), optionally one or more of a second component (e.g., optionally one or more components of type A), and optionally one or more of a third component (e.g., optionally one or more components of type C). In some embodiments, the item described by this phrase could include two or more of a first component (e.g., two or more components of type C (C1 and C2)), optionally one or more of a second component (e.g., optionally one or more components of type A), and optionally one or more of a third component (e.g., optionally one or more components of type B).

All numbers and ranges disclosed above may vary by some amount. Whenever a numerical range with a lower limit and an upper limit is disclosed, any number and any included range falling within the range is specifically disclosed. Unless defined otherwise, all technical and scientific terms used herein have the same meanings as commonly understood by one of skill in the art to which the disclosed invention belongs. If there is any conflict in the usages of a word or term in this specification and one or more patent or other documents that may be incorporated herein by reference, the definitions that are consistent with this specification should be adopted.

This written description uses examples to disclose the invention, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All citations referred herein are expressly incorporated by reference.

Apparatus

Provided herein are portable apparatus that can be used to analyze injection fluids. In one aspect, the disclosure relates to portable systems and methods of analyzing an injection fluid. In some embodiments, the injection fluid contains a polymer, but a polymer is not necessary. For example, the portable systems and methods may be used to determine viscosity, long term injectivity, filter ratio, or any combination thereof of the injection fluid.

The portable design of the apparatus can permit the apparatus to be readily transported to often remote locations (e.g., to sites in the field where injection fluids are being used) and used analyze injection fluids. In addition to improving portability, the relatively small footprint of the apparatus allows for the apparatus to be deployed in a wider variety of locales (e.g., in smaller rooms or facilities that lack the available space for a full scale analytical laboratory). This allows for once complex analytical operations to be efficiently performed on-site using a single, portable piece of equipment.

In some embodiments, the assembled portable apparatus can have a footprint of 25 $ft^2$ or less (e.g., 20 $ft^2$ or less, 15 $ft^2$ or less, 12.5 $ft^2$ or less, 10 $ft^2$ or less, 9 $ft^2$ or less, 8 $ft^2$ or less, 7 $ft^2$ or less, 6 $ft^2$ or less, 5 $ft^2$ or less, or 4 $ft^2$ or less). In some embodiments, the assembled portable apparatus can have a footprint of at least 2 $ft^2$ (e.g., at least 3 $ft^2$, at least 4 $ft^2$, at least 5 $ft^2$, or at least 6 $ft^2$).

The assembled portable apparatus can have a footprint ranging from any of the minimum values described above to any of the maximum values described above. For example, the assembled portable apparatus can have a footprint of from 2 $ft^2$ to 25 $ft^2$ (e.g., from 2 $ft^2$ to 15 $ft^2$, from 2 $ft^2$ to 10 $ft^2$, or from 4 $ft^2$ to 8 $ft^2$).

In some embodiments, the assembled portable apparatus can occupy a volume of 35 $ft^3$ or less (e.g., 30 $ft^3$ or less, 25 $ft^3$ or less, 20 $ft^3$ or less, 15 $ft^3$ or less, 12.5 $ft^3$ or less, 10 $ft^3$ or less, 9 $ft^3$ or less, 8 $ft^3$ or less, 7 $ft^3$ or less, 6 $ft^3$ or less, 5 $ft^3$ or less, or 4 $ft^2$ or less). In some embodiments, the assembled portable apparatus can occupy a volume of at least 2 $ft^3$ (e.g., at least 3 $ft^3$, at least 4 $ft^3$, at least 5 $ft^3$, at least 6 $ft^3$, at least 7 $ft^3$, or at least 8 $ft^3$).

The assembled portable apparatus can occupy a volume ranging from any of the minimum values described above to any of the maximum values described above. For example, the assembled portable apparatus can occupy a volume of from 2 $ft^3$ to 35 $ft^2$ (e.g., from 2 $ft^3$ to 15 $ft^3$, from 2 $ft^3$ to 10 $ft^3$, or from 2 $ft^3$ to 8 $ft^3$).

The components of the apparatus can be self-contained and assembled within a housing. This allows for the apparatus to be rapidly deployed. For example, setup times can be short enough to allow the portable up and running in a matter of hours. This is significantly shorter than the setup time required for a typical full scale analytical laboratory.

Referring now to FIG. 1, the portable apparatus (10) can comprise a housing (12) encompassing one or more components of the portable apparatus. The components of the portable apparatus can comprise an inlet (14) to receive the injection fluid; a pre-filter (16) coupled to the inlet (14); a pump (20) coupled to the pre-filter (16) to direct the injection fluid from the pre-filter (16) through one or more analytical modules (22) chosen from a surrogate core, a capillary viscometer, a filter, or a combination thereof; one or more pressure transducers (32, 34) chosen from a pressure transducer coupled to the pre-filter (32), a pressure transducer coupled to any of the one or more analytical modules (34), or a combination thereof; a data acquisition system (DAS, 26) that receives data from the one or more pressure transducers (32, 34) and calculates a property of the injection fluid from the data; and a power supply (24) coupled to the pump (20), the one or more pressure transducers (32, 34), and the data acquisition system (26) to provide power. Depending upon the identity of the one or more analytical modules included in the apparatus, the can be used to determine the long term injectivity of the injection fluid, the viscosity of the injection fluid, the filter ratio of the injection fluid, or any combination thereof. In some embodiments, the DAS (26) can be coupled to an external computing system (28) that receives data from the DAS (26) and controls the pump (20). Optionally, one or more additional pre-filters (36) can be interposed between inlet 14 and pre-filter 16. A pressure transducer coupled (38) can also be coupled to the one or more additional pre-filters (36).

Figure 2:
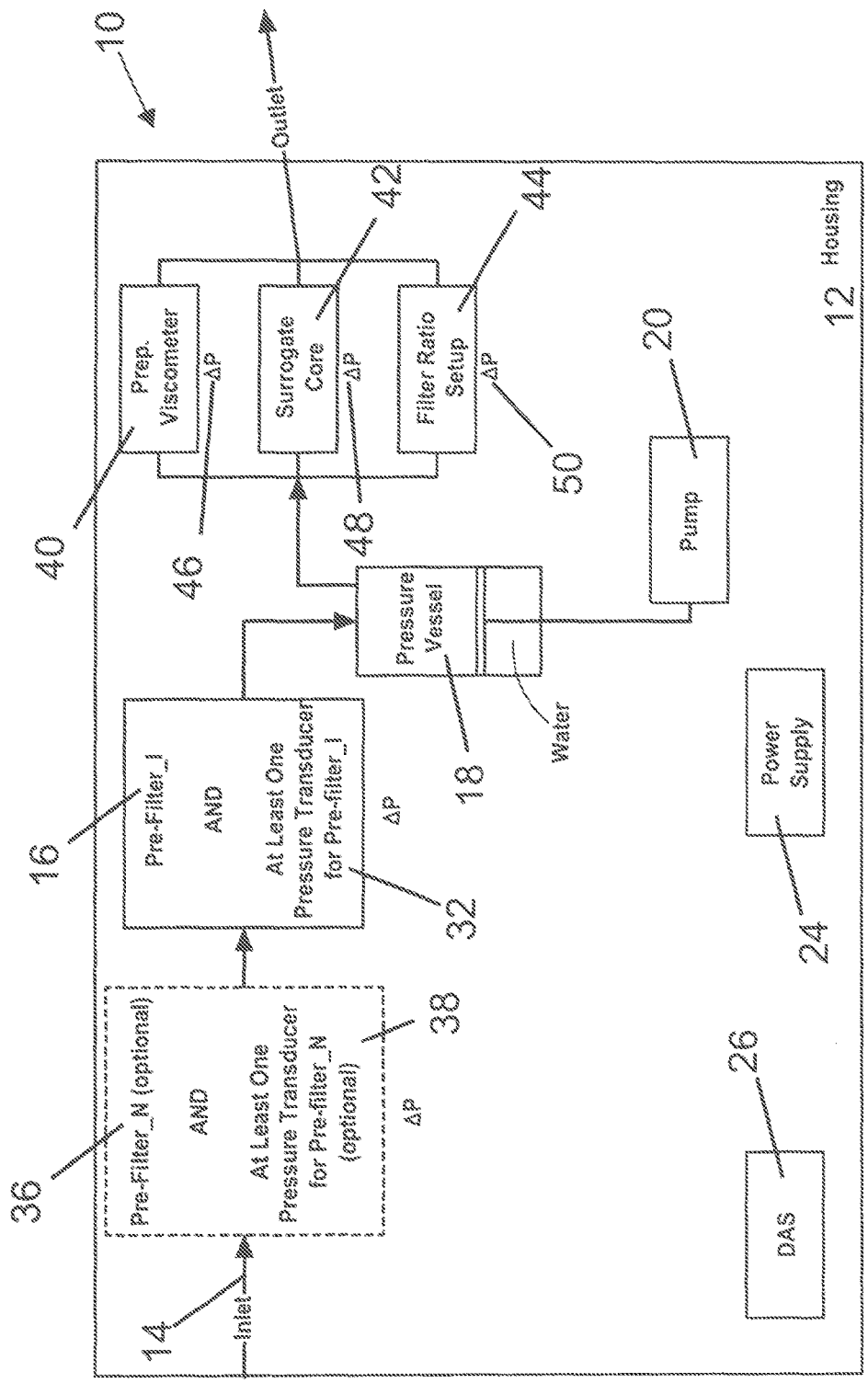
FIG. 2 is a schematic illustration of the components of a portable apparatus for analyzing an injection fluid.

In some embodiments, the components of the portable apparatus (10) can comprise two or more analytical modules (22) chosen from a surrogate core, a capillary viscometer, a filter, or a combination thereof. In these embodiments, the pump (2) can be coupled to the pre-filter (16) to direct the injection fluid from the pre-filter (16) through the two or more analytical modules (22). In some embodiments, the two or more analytical modules can be arranged in parallel within the device, such that injection fluid f Referring now to FIG. 2, in certain embodiments, the components of the portable apparatus comprise three analytical modules (40, 42, 44). The three analytical modules comprise a surrogate core (42), a capillary viscometer (40), and a filter (44). In these embodiments, the pump (20) can be coupled to the pre-filter (16) to direct the injection fluid from the pre-filter (16) through the three analytical modules (40, 42, 44). In certain of these embodiments, the one or more pressure transducers can comprise a pressure transducer coupled to the pre-filter to measure a differential pressure of the injection fluid across the pre-filter (32), a pressure transducer coupled to the surrogate core to measure a differential pressure of the injection fluid across the surrogate core (48), a pressure transducer coupled to the capillary viscometer to measure a differential pressure of the injection fluid across the capillary viscometer (46), and a pressure transducer coupled to the filter to measure an absolute pressure of the injection fluid to be filtered through the filter (50). In these embodiments, the apparatus can be used to simultaneously determine the long term injectivity, viscosity, and filter ratio of an injection fluid.

Referring now again to FIG. 1, in some cases, the apparatus can further comprise a pressure vessel (18) coupled to the pre-filter (16) to receive and store injection fluid from the pre-filter. The pressure vessel can further be coupled to the one or more analytical modules (22) to deliver the injection fluid from the pressure vessel (18) to the one or more analytical modules (22). The pump (20) can be coupled to the pressure vessel (18) to pump the injection fluid through the pressure vessel (18).

In some embodiments, the apparatus can further comprise additional analytical modules (22), such as a temperature probe, a pH probe, a conductivity probe, an oxidation reduction potential probe, or a combination thereof. This in some embodiments, the apparatus can include 2, 3, 4, 5, 6, 7, 8, 9, 10, or more analytical modules. When a plurality of modules are present in the apparatus, the modules can be coupled in series with respect to one another (e.g., such that the injection fluid is directed through the modules sequentially), in parallel with one another (e.g., such that the injection fluid branches into two separate streams, each of which is directed through one of the modules), or a combination thereof.

In some embodiments, the one or more analytical modules are each releasably connected to the portable apparatus. This can allow the analytical modules to be readily swapped in and out of the portable apparatus (e.g., to allow for cleaning and repair, or to include the particular combination of modules needed to measure a desired combination of properties of the injection fluid). In certain embodiments, the one or more analytical modules can each individually be enclosed within a housing.

The components of the portable apparatus (e.g., the inlet, the pre-filter, the one or more analytical modules, and the pressure vessel) together form a closed path for fluid flow from the inlet to the one or more analytical modules. Using this design, the injection fluid processed by the device can be maintained in a reduced environment (e.g., without significant oxidative degradation occurring) until after is has been processed by the analytical modules. As a consequence, the properties measured by the analytical modules can accurately reflect the properties of the injection fluid upon injection into an injection well.

Figure 3A:
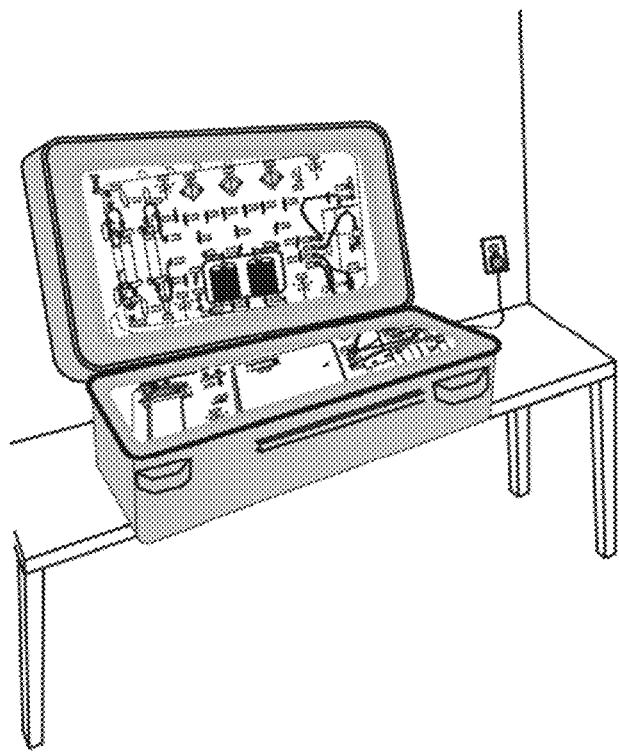
FIG. 3A is a perspective rendering of an example assembled portable apparatus positioned for use on a tabletop.
Figure 3B:
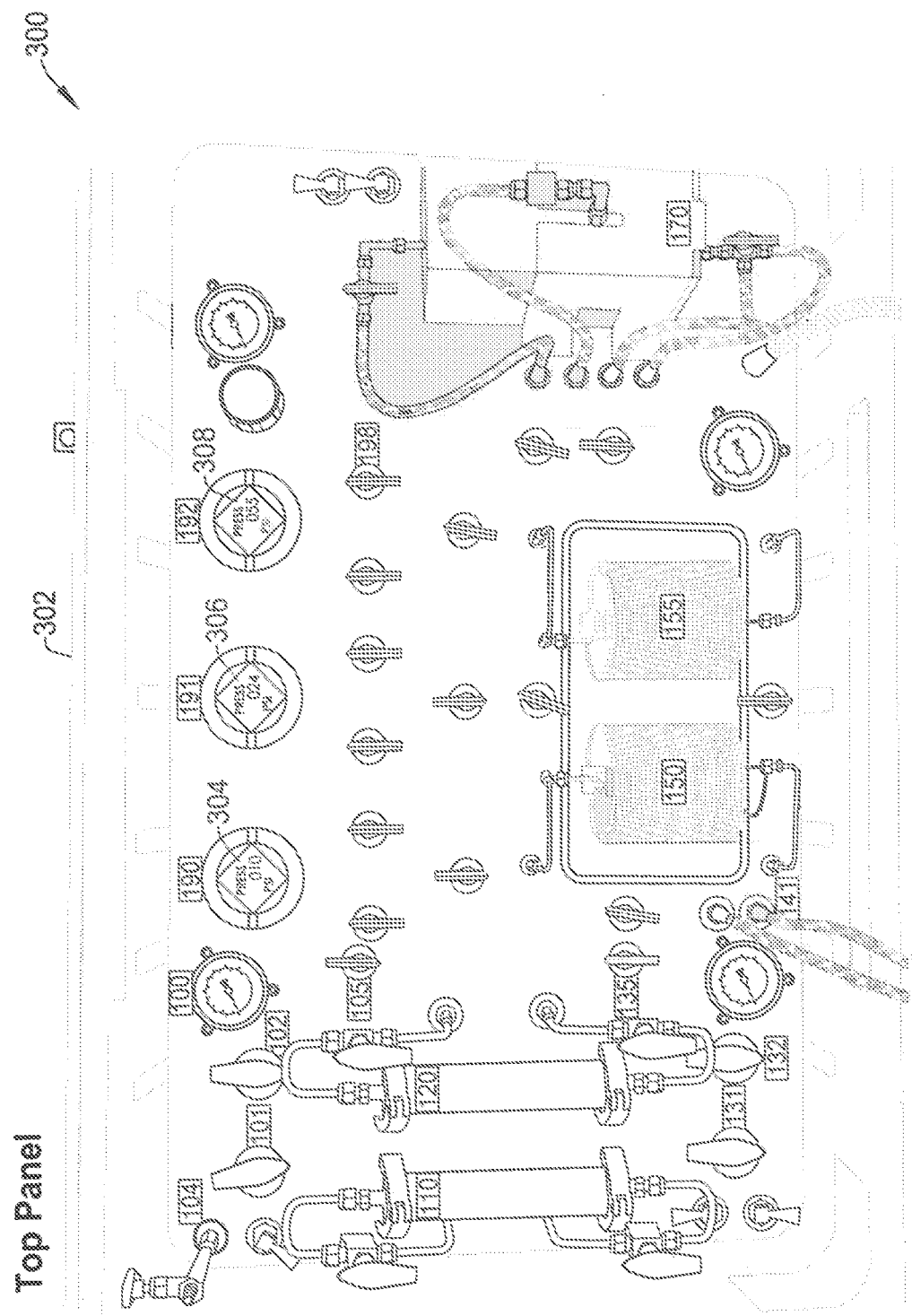
FIG. 3B is an enlarged perspective rendering of the top panel of the portable apparatus shown in FIG. 3A.
Figure 3C:
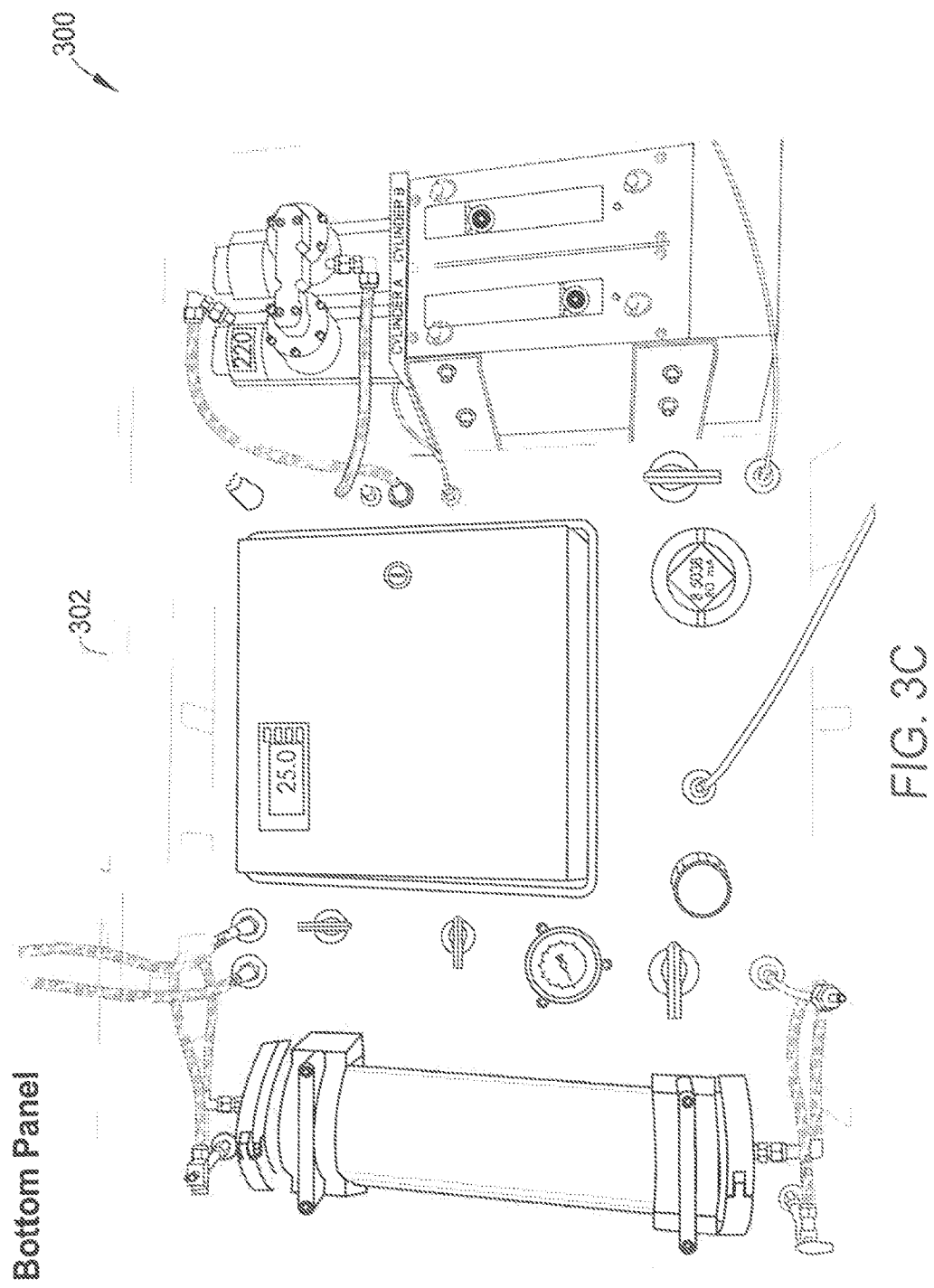
FIG. 3C is an enlarged perspective rendering of the top panel of the portable apparatus shown in FIG. 3A.
Figure 4:
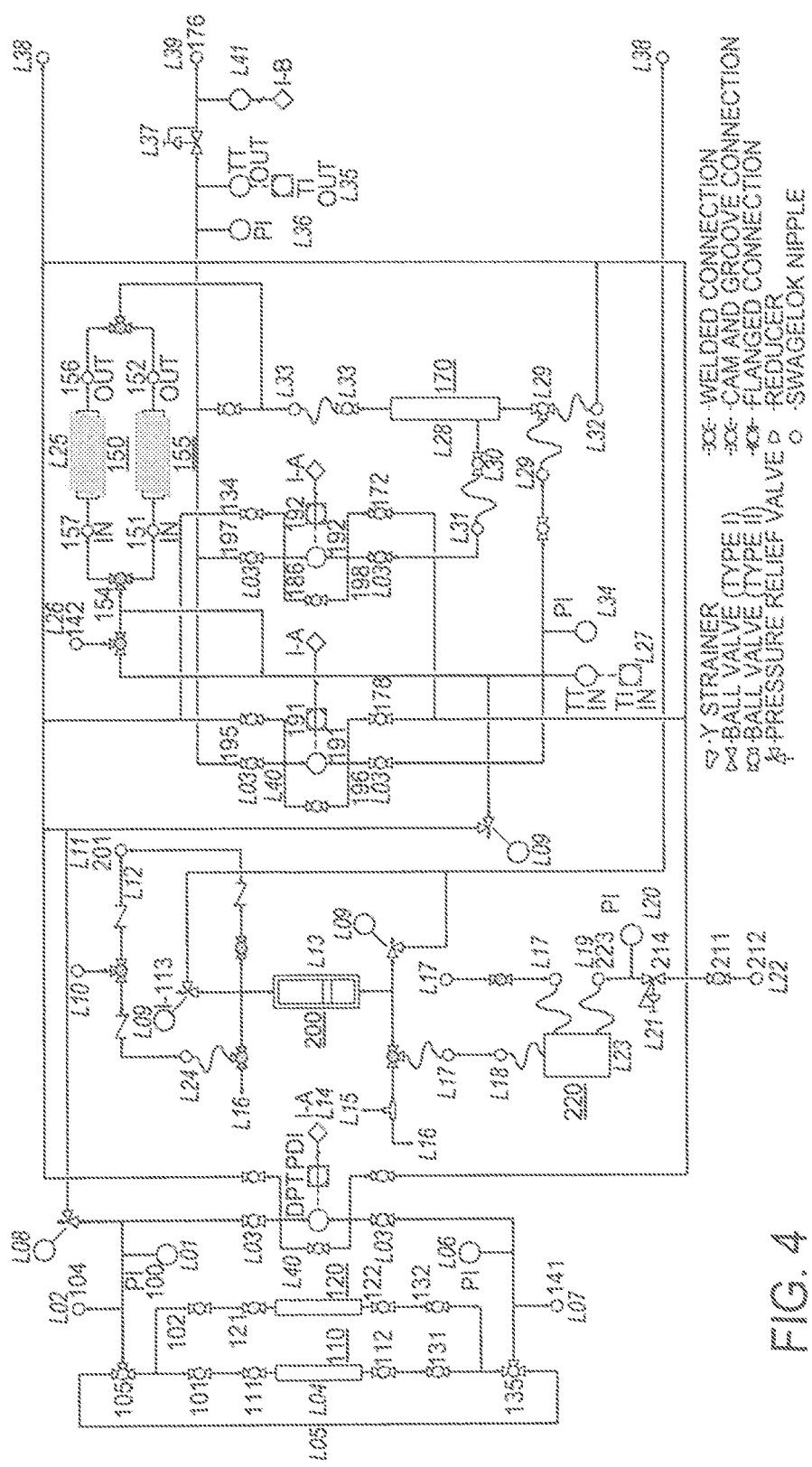
FIG. 4 is a schematic illustration of the components of the portable apparatus for analyzing an injection fluid shown in FIGS. 3A-3C.
Figure 5:
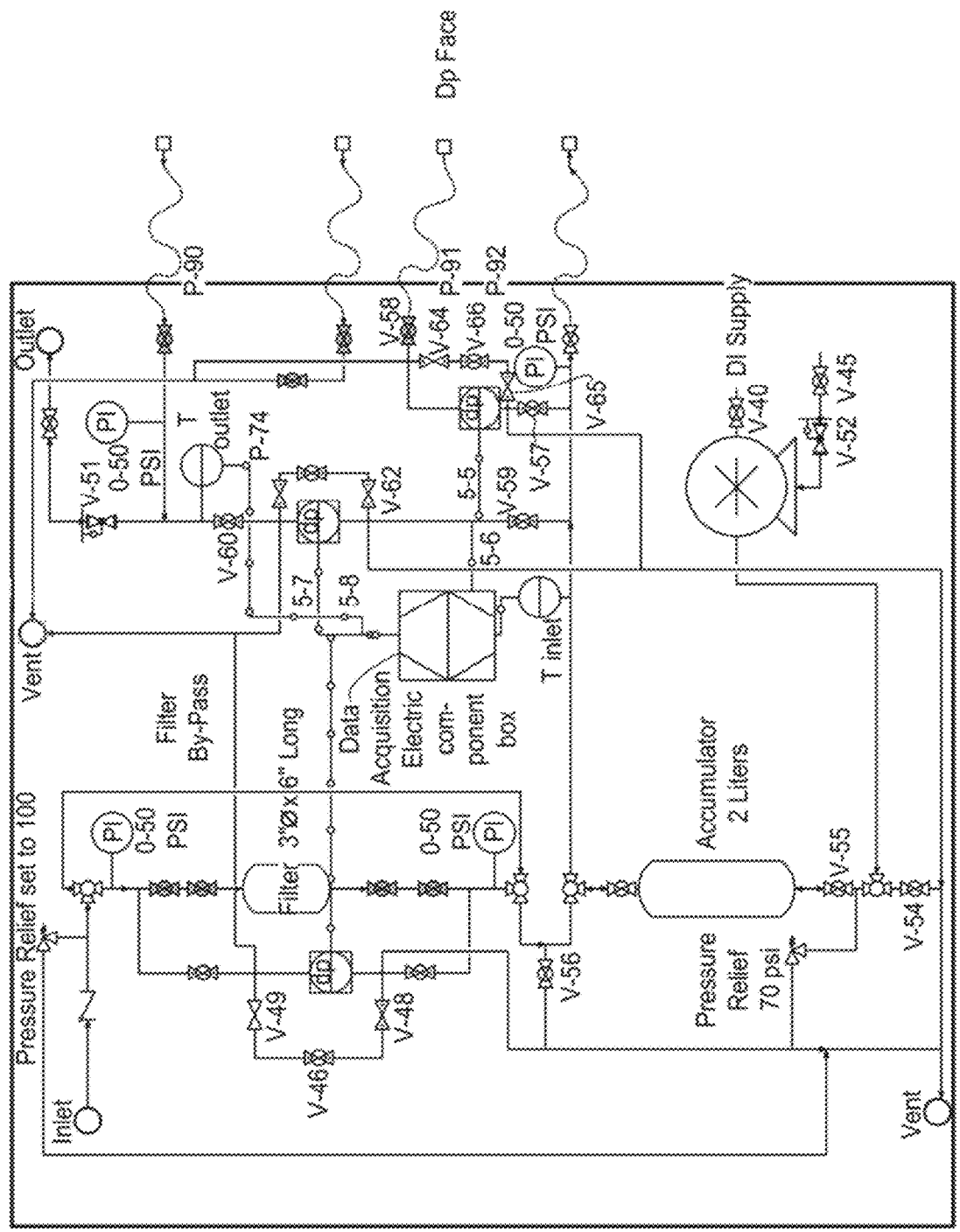
FIG. 5 is a schematic illustration of an alternative embodiment of a portable apparatus for analyzing an injection fluid.

Referring now to FIG. 3B, FIG. 3C, and FIG. 4, in some embodiments, the portable apparatus (300) can comprise an inlet port (104) to allow injection fluid (e.g., injection fluid containing a polymer, injection fluid not containing a polymer, injection fluid containing only brine, etc.) from a fluid flow line or conduit, a sample vessel, or a container to enter the apparatus. The pressure of the injection fluid entering the apparatus can be regulated to less than about 75 psig, which can be displayed on at least one pressure gauge (100). The pressure is regulated using the pump (220) described in subsequent sections, a pressure regulator, a control valve and a vent port, a pressure relief valve, or any combination of these or other devices.

The injection fluid is then routed through at least one filter (110, 120). The filter body may be filled with coarse sand, which acts as a filter medium for the injection fluid. In some embodiments, ball valves (101, 102, 105, 111, 112, 121, 122, 131, 132, 135) may be used to isolate multiple filters (110, 120) from the inlet of the apparatus. A pressure relief device can be mounted to the inlet line upstream of the filter(s) to vent excess pressure in case of a filter blockage. At least one differential pressure transducer can be used to monitor pressure across the filter(s). The pressure can depend on the pressure rating of the devices, etc.

The outlet of the filter (141) is connected to the inlet of a pump (e.g., a piston or syringe type pump). In certain applications where the pump and the injection fluid are incompatible, a pressure vessel with a piston may be used to allow the pump to pump water, mineral oil, or another benign liquid and still provide flow control to the injection fluid in the pressure vessel. The pump has a pressure relief device to vent excess pressure in case of a blockage or inadvertent valve closure.

Downstream of the pump is a switching valve. This directs flow to one of three devices: at least one capillary viscometer (150, 155), at least one surrogate core (170), and at least one filter to measure a filter ratio (L15). At least one differential pressure transducer is used to measure the pressure across the capillary viscometer (191) and the surrogate core (192).

The capillary viscometer (150, 155) is used to measure viscosity of the injection fluid inline without exposing it to oxygen. The viscometer comprises a stainless steel coil of tubing that is at least 25 feet long and at least ¹⁄₁₆-inch in diameter. In some embodiments, the coil of tubing may be at least 50 feet long. In some embodiments, the coil of tubing may be at least 100 feet long. In some embodiments, the diameter of the coil of tubing may be at least ⅛-inch in diameter. In some embodiments, the diameter of the coil of tubing may be at least ¼-inch in diameter. The injection fluid flows through it at a constant rate controlled by the pump. The differential pressure across the capillary tube is measured using at least one differential pressure transducer. At least one pressure relief device is used to vent excess pressure in the event of a plugged capillary tube.

The surrogate core (170) may be at least four inches in length, at least 1.5 inches in diameter, and encased in a two-part epoxy capable of withstanding up to 100 psig line pressure. In one embodiment, the surrogate core may be at least 6 inches in length and at least 2 inches in diameter. The surrogate core has an inlet, an outlet, and at least one pressure tap (L30) two inches past the inlet. The injection fluid flows through the surrogate core at a constant rate controlled by the pump. At least one differential pressure transducer (192) is used to measure pressure across the surrogate core (between inlet and outlet) and at least one pressure transducer is used to measure pressure across the injection face of the surrogate core (between inlet and pressure tap two inches past the inlet). A back pressure regulator is used to keep the core at a minimum pressure of 5 psig to prevent accidental introduction of oxygen into the surrogate core.

The modified filter ratio test is performed using the pump in a constant pressure mode. The injection fluid from the pump is sent through a 1.2 micron 47 mm or 90 mm polycarbonate filter with a driving pressure of 15 psig. The flow rate of the filtrate is measured over time. The flow rate can be measured by recording volume at specific time increments or by recording the weight of the filtrate at specific time increments. Weight can be recorded using a digital balance with data collected by the data acquisition system (DAS). The time increment range can be at least once per second to at least once per minute.

The injection fluid also passes through a port with at least one pH probe, at least one thermocouple (temperature probe), at least one conductivity probe, at least one Oxidation-Reduction Potential (ORP) probe, or any combination of the four.

The pump, pressure transducers, pH, ORP, conductivity probe, and temperature probes are all powered from a power source built into the apparatus. All these instruments acquire data through a data acquisition system (DAS) and associated power supply. The DAS is connected to at least one computing system (e.g., computer) with software to control the pump and to monitor the data generated by the devices listed earlier. The computing system may be internal to the portable apparatus or external to the portable apparatus.

In one embodiment, a computing system includes a processor communicatively connected to a memory via a data bus. The processor can be any of a variety of types of programmable circuits capable of executing computer-readable instructions to perform various tasks, such as mathematical and communication tasks (e.g., calculation of the long term injectivity of the injection fluid, calculation of the viscosity of the injection fluid, calculation of the filter ratio of the injection fluid, or any combination thereof). The computing system may be a computer, a wireless device, a wired device, a plurality of networked devices, etc.

The memory can include any of a variety of memory devices, such as using various types of computer-readable or computer storage media. A computer storage medium or computer-readable medium may be any medium that can contain or store the program for use by or in connection with the instruction execution system, apparatus, or device. By way of example, computer storage media may include dynamic random access memory (DRAM) or variants thereof, solid state memory, read-only memory (ROM), electrically-erasable programmable ROM, optical discs (e.g., CD-ROMs, DVDs, etc.), magnetic disks (e.g., hard disks, floppy disks, etc.), magnetic tapes, and other types of devices and/or articles of manufacture that store data. Computer storage media generally includes at least one or more tangible media or devices. Computer storage media can, in some embodiments, include embodiments including entirely non-transitory components. In the embodiment shown, the memory stores an injection fluid analysis application, discussed in further detail below.

The computing system can also include a communication interface configured to receive data such as at least a portion of the data generated by the devices of the apparatus, etc. Other data may be received via the communication interface. The communication interface may also be configured to transmit data or other functionality.

Additionally, a display can be used for presenting a user interface associated with the injection fluid analysis application. In various embodiments, the computing system can include additional components, such as peripheral I/O devices, for example, to allow a user to interact with the user interface associated with the injection fluid analysis application. For example, the display and the peripheral I/O devices may allow a user to provide user input, view and edit settings, manipulate data, or other functionality. In some embodiments, the user may even provide at least a portion of the data via the user interface.

In various embodiments, the computing system may allow for interaction with at least one other software item, at least one other hardware item, or both that are available from a third party. In short, those of ordinary skill in the art will appreciate that various modifications may be made and the scope of the claims is not limited to the discussion herein. For example, those of ordinary skill in the art will appreciate that the inventive principles may be implemented using automated steps only or using a combination of automated steps and manual steps.

In one embodiment, the computing system is a laptop that is external to the portable apparatus and it controls the pump, receives data from the DAS that is internal to the portable apparatus, and displays data to a user.

Embodiments of the present disclosure can be implemented as a computer process (method), process (method), a computing system, or as an article of manufacture, such as a computer program product or computer readable media. The term computer readable media as used herein may include computer storage media. Computer storage media may include volatile and nonvolatile, removable and non-removable media implemented in any method or technology for storage of information, such as computer readable instructions, data structures, or program modules. Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing system 1000, above. Computer storage media does not include a carrier wave or other propagated or modulated data signal. In some embodiments, the computer storage media includes at least some tangible features; in many embodiments, the computer storage media includes entirely non-transitory components.

Returning to the portable apparatus, the apparatus also comprises at least one pressure regulator to regulate the supply of dry air, nitrogen, argon, or any other non-flammable, non-corrosive, non-toxic gas to the pump to operate gas operated valves. This gas supply is also used to purge the flow system and to leak test the apparatus.

The apparatus is housed in a weather proof container (302). The apparatus is powered by a single power cable supplying power to the DAS and associated power supply. In one embodiment, the apparatus can be made using intrinsically safe, explosion proof electrical connections and devices.

In an alternative embodiment, the gas supply can also be used to provide a constant source of pressure to a pressure vessel. The injection fluid in the pressure vessel can then be routed through the surrogate core, the capillary viscometer, or the filter at a constant pressure and the rate measured by recording the volume collected over time or the weight of the injection fluid collected over time. This alternative embodiment avoids a pump completely, and it also avoids a pressure vessel with a piston in it.

Additional Embodiments

In some embodiments, a portable apparatus for analyzing an injection fluid comprises a housing. The housing comprises at least one inlet, at least one pre-filter, at least one pressure vessel, at least one pump, at least one power supply, at least one pressure transducer, and at least one pressure tap, as well as the following: at least one surrogate core for determining long term injectivity of the injection fluid, at least one capillary viscometer for determining viscosity of the injection fluid, at least one filter for determining a filter ratio of the injection fluid, at least one pH probe for determining pH of the injection fluid, at least one oxidation reduction potential probe for determining oxidation reduction potential of the injection fluid, at least one temperature probe for determining temperature of the injection fluid, at least one conductivity probe for determining conductivity of the injection fluid, or any combination thereof. The portable apparatus may be utilized to analyze practically any injection fluid, and in some embodiments, the injection fluid may comprise a polymer, a solvent, an optional additive, or any combination thereof.

Housing:

A housing may be practically any housing configured to protect the portions of the portable apparatus. The housing may be weatherproof in some embodiments. In some embodiments, the housing has one or more of these characteristics: rigid, mounted on casters, lockable, weather tight when closed, lightweight, may be made of metal, plastics including fiber reinforced plastics, large enough to be able to enclose all the required and some optional parts. A commercially available example of the housing may be a Pelican Case™.

Inlet:

An inlet may be practically any inlet configured to receive the injection fluid. In some embodiments, the inlet has one or more of these characteristics: ¼-inch to ½-inch tubing or pipe connection on the outside of the case with a protective cap or plug. A commercially available example of the inlet may be a Swagelok® bulkhead fitting with a protective cap.

Pre-filter:

A pre-filter may be practically any filter configured to collect solids and immiscible liquids from the injection fluid, and may include, for example, coarse sand. The pre-filter may include multiple filters in series in some embodiments and the injection fluid passes through the multiple filters. In some embodiments, the pre-filter has one or more of these characteristics: a stainless steel cylinder ½-inch to 2-inches in diameter with isolation valves on both ends, and containing a well sorted sand pack or ceramic beads, glass beads, plastic beads and two to ten stainless steel mesh disks at each end. A commercially available example of the pre-filter may be a High Performance Liquid Chromatography column.

Pressure Vessel:

A pressure vessel may be practically any pressure vessel configured to deliver the injection fluid. An accumulator may be used instead of the pressure vessel in some embodiments. In some embodiments, the pressure vessel has one or more of these characteristics: a stainless steel, titanium, metal alloy, plastic or glass column rated to the pressures expected for the test, air tight seals on either end, supply and discharge valves and containing a floating piston made of metal or plastic such as Teflon™. A commercially available example of the pressure vessel may be an accumulator or a Fluid Transfer Vessel for sale by Core Laboratories.

Pump:

A pump may be practically any pump configured to pump the injection fluid through the pressure vessel. A vacuum pump and gas cylinder (or gas line) may be used instead of the pump in some embodiments. In some embodiments, the pump has one or more of these characteristics: syringe type positive displacement pump with the ability to run at constant rate and constant pressure and with a variable inflow and outflow rate. A commercially available example of the pump may be a Teledyne ISCO™ 500D or a Quizix QX™ type.

Power Supply:

A supply may be practically any device configured to provide power to the pump and each pressure transducer. In some embodiments, the power supply has one or more of these characteristics: 120V, 60 Hz AC power supply for the pump and other devices such as a computer and a transformer providing 12 or 24 volt direct current supply for instrumentation.

Surrogate Core:

A surrogate core may be practically any surrogate core for determining long term injectivity of the injection fluid. In some embodiments, the surrogate core has one or more of these characteristics: a cylindrical piece of outcrop rock from a commercial quarry such as Berea rock with known values of permeability, porosity and mineralogy.

Capillary Viscometer:

A capillary viscometer may be practically any capillary viscometer for determining viscosity of the injection fluid. In some embodiments, the capillary viscometer has one or more of these characteristics: a fixed, small diameter (1/16-inch to ¼-inch) tube of a known long length (30 feet to 100 feet) with the ability to measure the pressure differential across the tube using a differential pressure transducer and a temperature sensor.

Filter:

A filter may be practically any filter for determining a filter ratio of the injection fluid. In some embodiments, the filter is a 1.2 micron polycarbonate filter having a diameter of 47 mm or 90 mm. The injection fluid is considered to have passed if it satisfies a filter ratio of 1.5 or less at 15 psi using the 1.2 µm filter having the diameter of 47 mm or 90 mm.

In some embodiments, the filter is a 1.2 micron 47 mm polycarbonate filter of Millipore™.

Pressure Transducer:

A pressure transducer may be practically any pressure transducer or gauge configured to determine pressure. In some embodiments, the pressure transducer may be used to determine absolute pressure. In some embodiments, the pressure transducer may be used to determine a differential pressure. For example, a single pressure transducer (e.g., a single differential pressure transducer that determines a pressure difference between two points) may be utilized for determining the differential pressure. In one embodiment, a first pressure transducer may be installed at a first location and a second pressure transducer may be installed at a second location for determining the differential pressure. The pressure transducer may be analog in some embodiments. The pressure transducer may be digital in some embodiments. The pressure transducer may include a built in display (304, 306, 308). The pressure transducer may include an external display and the power supply provides power to the external display. A commercially available example of the pressure transducer may be a pressure transducer manufactured by Rosemount.

In some embodiments, at least one pressure transducer may be coupled to the pre-filter for determining a differential pressure across the pre-filter as the injection fluid flows through the pre-filter. In some embodiments, at least one pressure transducer is coupled to the surrogate core for determining a differential pressure across the surrogate core as the injection fluid flows through the surrogate core. In some embodiments, at least one pressure transducer is coupled to the capillary viscometer for determining a differential pressure across the capillary viscometer as the injection fluid flows through the capillary viscometer. In some embodiments, at least one pressure transducer is coupled to the filter for determining an absolute pressure of the injection fluid to be filtered through the filter. Those of ordinary skill in the art will appreciate that some embodiments may not require all of the pressure transducers that are discussed herein.

Pressure Tap:

A pressure tap may be practically any pressure tap for determining pressure across an injection face of the surrogate core. In some embodiments, the pressure tap includes a port along the length of the core to allow a pressure measurement across the first two inches of the core.

In some embodiments, the surrogate core further includes at least one pressure tap for determining pressure across an injection face of the surrogate core. Those of ordinary skill in the art will appreciate that some embodiments may not require the pressure tap discussed herein.

pH Probe:

A pH probe may be practically any in-line pH probe for determining pH of the injection fluid in a flow through port. In some embodiments, the pH probe may include a temperature probe or temperature capability, thus, a separate temperature probe may not be needed in some embodiments.

Oxidation Reduction Potential Probe:

An oxidation reduction potential (ORP) probe may be practically any in-line oxidation reduction potential probe for determining oxidation reduction potential of the injection fluid. Of note, the oxidation reduction potential probe may be a T shape in some embodiments, and it may be placed before or after practically any item in the housing. However, those of ordinary skill in the art may appreciate that the oxidation reduction potential should not be near oxygen.

Temperature Probe:

A temperature probe may be practically any in-line temperature probe for determining temperature of the injection fluid. In some embodiments, the pH probe may include a temperature probe or temperature capability, thus, a separate temperature probe may not be needed in some embodiments. The temperature probe may be placed before or after practically any item in the housing.

Conductivity Probe:

A conductivity probe may be practically any in-line conductivity probe for determining conductivity of the injection fluid.

Those of ordinary skill in the art will appreciate that some embodiments may not require all of the items discussed herein. For example, those of ordinary skill in the art will appreciate that some embodiments may not require the surrogate core, the capillary viscometer, the filter, the pH probe, the oxidation reduction potential probe, the temperature probe, and the conductivity probe.

Indeed, in some embodiments, each of the surrogate core, the capillary viscometer, the filter, the pH probe, the oxidation reduction potential probe, the temperature probe, and the conductivity probe may be treated as an analysis component, and analysis components may be installed in or removed from the housing depending on the analysis to be performed on the injection fluid. Any analysis component to be used to analyze the injection fluid remains in the housing and any analysis component that will not be used to analyze the injection fluid is removed from the housing. For example, the surrogate core may be an analysis component that is removable from the housing. The capillary viscometer may be an analysis component that is removable from the housing. The filter may be an analysis component that is removable from the housing. The pH probe may be an analysis component that is removable from the housing. An oxidation reduction potential probe may be an analysis component that is removable from the housing. The temperature probe may be an analysis component that is removable from the housing. The conductivity probe may be an analysis component that is removable from the housing. Those of ordinary skill in the art will appreciate that this is not an exhaustive list of analysis components that can be installed in the portable apparatus. By using removable analysis components, fewer valves, bypasses, connections, etc. may be used, which reduces the complexity of the portable apparatus. Furthermore, by using removable analysis components, the weight of the portable apparatus may be reduced to make it easier to move the portable apparatus to different locations, such as different locations on an offshore platform.

In some embodiments, each of the surrogate core, the capillary viscometer, the filter, the pH probe, the oxidation reduction potential probe, the temperature probe, and the conductivity probe is an analysis component, and the injection fluid flows from the pressure vessel through a plurality of the analysis components in series. For example, the portable apparatus may include the capillary viscometer analysis component and the surrogate core analysis component coupled in series, but the other analysis components have been removed from the housing. Thus, in this example, the injection fluid flows from the pressure vessel through the capillary viscometer and then through the surrogate core. In a second example, the portable apparatus may include the capillary viscometer analysis component and the filter analysis component coupled in series, but the other analysis components have been removed from the housing. Thus, in this second example, the injection fluid flows from the pressure vessel through the capillary viscometer and then through the filter. In a third example, the injection fluid flows from the pressure vessel through the capillary viscometer analysis component, the surrogate core analysis component, the filter analysis component, or any combination thereof and then the injection fluid flows through the pH probe analysis component, the oxidation reduction potential probe analysis component, or any combination thereof.

In some embodiments, each of the surrogate core, the capillary viscometer, the filter, the pH probe, the oxidation reduction potential probe, the temperature probe, and the conductivity probe is an analysis component, and wherein the injection fluid flows from the pressure vessel through a plurality of the analysis components in parallel. For example, the portable apparatus may include the capillary viscometer analysis component and the surrogate core analysis component in parallel, but the other analysis components have been removed from the housing. Thus, in this example, the injection fluid flows from the pressure vessel through the capillary viscometer and the surrogate core in parallel. In a second example, the portable apparatus may include the capillary viscometer analysis component and the filter analysis component in parallel, but the other analysis components have been removed from the housing. Thus, in this second example, the injection fluid flows from the pressure vessel through the capillary viscometer and the filter in parallel. Those of ordinary skill in the art will appreciate that "in parallel" may include flowing at about the same time or flowing approximately simultaneously in some embodiments.

In short, those of ordinary skill in the art will appreciate that the portable apparatus may have a flexible arrangement. For example, the pressure vessel may have at least one port and different analysis components may be coupled to that the port depending on the analysis to be performed on the injection fluid.

Those of ordinary skill in the art will also appreciate that some embodiments may include additional items. For example, in some embodiments, the portable apparatus may include a data acquisition system (DAS) internal to the housing. The DAS is coupled to the power supply to receive power, and the DAS is coupled to each pressure transducer to receive data from each pressure transducer. The data from each pressure transducer received by the DAS comprises digital signals, and the DAS converts the digital signals to analog signals. Some embodiments may also include a computing system external to the housing. The computing system is coupled to the DAS (e.g., wirelessly or wired), and the computing system receives the analog signals from the DAS and converts the analog signals into pressure values. The computing system may also store the pressure values, display the pressure values, or both.

The computing system uses the pressure values to determine the long term injectivity of the injection fluid, the viscosity of the injection fluid, the filter ratio of the injection fluid, a change in permeability, a reduction in permeability, or any combination thereof. For example, the computing system may use Darcy's law, as well as any data accessible by the computing system (e.g., data received from the DAS, data from memory or other storage of the computing system, data from practically any other computing system coupled or networked with the computing system, etc.), for determining viscosity. For example, the computing system may use relative permeability, a pressure drop, or any combination thereof, as well as any data accessible by the computing system, for determining long term injectivity. For example, the computing system may use the equations provided herein, as well as any data accessible by the computing system, for determining the filter ratio. For example, the computing system may compare differential pressure at various points in time, as well as use any data accessible by the computing system, to determine if there is a change or a reduction in permeability. Equations and other information for some of these items are provided in Polymer-Improved Oil Recovery by K. S. Sorbie, published in 1991, which is incorporated herein by reference in its entirety.

In some embodiments, the portable apparatus may include a data acquisition system (DAS) internal to the housing to receive data and a computing system that is external to the housing. The DAS provides data to the computing system, either wired or wireless. The computing system uses the data to determine the long term injectivity of the injection fluid, the viscosity of the injection fluid, the filter ratio of the injection fluid, a change in permeability, a reduction in permeability, or any combination thereof. The computing system may also use the data to generate an alert in response to the data exceeding a threshold, uses the data to control operation of the pump, or any combination thereof. The computing system may also store the data, display the data, or both. The computing system may also identify patterns, generate predictions, monitor or track pressures or other items, generate plots of various items, etc. using the data that is accessible to computing system.

Turning more specifically to the pump, in some embodiments, the portable apparatus may include a data acquisition system (DAS) internal to the housing. The DAS is coupled to the power supply to receive power, and the DAS is coupled to the pump. The DAS receives pump data from the pump. Pump data includes data regarding whether or not the pump is running, flow rate, etc. Some embodiments may also include a computing system external to the housing. The computing system is coupled to the DAS, and the computing system receives the pump data from the DAS. Additionally, or alternatively, in some embodiments, the computing system that is external to the housing provides data to the pump, either wired or wireless. The data provided to the pump by the computing system external to the housing controls operation of the pump (e.g., provides an indication to shut off the pump if the computing system detects data that exceeds a threshold).

In some embodiments, the portable apparatus may include data acquisition system (DAS) internal to the housing. The DAS is coupled to the power supply to receive power, and the DAS is coupled to each pressure transducer to receive data from each pressure transducer. The data comprises differential pressure data. Some embodiments may also include a computing system external to the housing. The computing system is coupled to the DAS (e.g., wirelessly or wired). The computing system receives the differential pressure data from the DAS. The computing system may use the differential pressure data is described herein, for example, for equations, comparisons, alerting, controlling, plotting, monitoring or tracking, storing, displaying, etc.

In some embodiments, the portable apparatus may include a data acquisition system (DAS) internal to the housing to receive data and a computing system that is external to the housing. The DAS receives data from the computing system, either wired or wireless.

Methods of Use

On-Site Analysis of Injection Fluid:

Also provided herein are methods of analyzing injection fluids using the apparatus described herein. If desired, the portable nature of the apparatus allows the apparatus to be used to analyze an injection fluid onsite at or near an injection well. In one example, the injection fluid may be mixed and it then flows towards a wellbore (e.g., an injection wellbore, a hydraulic fracturing wellbore, etc.). As the injection fluid flows towards the wellbore, one or more samples of the injection fluid may be collected and placed in the inlet of the portable apparatus for analysis. The sample of the injection fluid may be manually collected by personnel. Alternatively, an injection fluid line may be connected directly to the inlet of the portable apparatus for analysis of the injection fluid.

In some cases, the apparatus can be used to perform continuous and/or real-time measurements of properties of injection fluids, including the long term injectivity, viscosity, and filter ratio of an injection fluid. This information can be used to monitor the characteristics of an injection fluid over time, allowing technicians to rapidly correct any deficiencies in the as-prepared injection fluid as compared to a specified target composition. This can be implemented, for example, as part of a quality assurance program associated with an oil and gas operation, such as hydrocarbon recovery. The hydrocarbon recovery can comprise an enhanced oil recovery (EOR) operation, such as a polymer flooding operation, an AP flooding operation, a SP flooding operation, an ASP flooding operation, a conformance control operation, a hydraulic fracturing operation, or any combination thereof.

Accordingly, also provided or methods for hydrocarbon recovery that employ the apparatus described herein to measure and/or monitor the properties of an injection fluid utilized during the hydrocarbon recovery process. These methods for hydrocarbon recovery can comprise (a) providing a subsurface reservoir containing hydrocarbons there within; (b) providing a wellbore in fluid communication with the subsurface reservoir; (c) mixing an injection fluid and flowing the injection fluid through a fluid conduit to the wellbore; (d) measuring a property of the injection fluid flowing through the fluid conduit using a portable apparatus described herein; and (e) injecting the injection fluid through the wellbore into the subsurface reservoir. The inlet of the portable apparatus can be fluidly connected to the fluid conduit, thereby forming a closed path for fluid flow from the fluid conduit to the one or more analytical modules in the portable apparatus. This ensures that the fluid remains in a reduced environment until after is has been processed by the analytical modules. As a consequence, the properties measured by the analytical modules can accurately reflect the properties of the injection fluid upon injection into an injection well.

Figure 6:
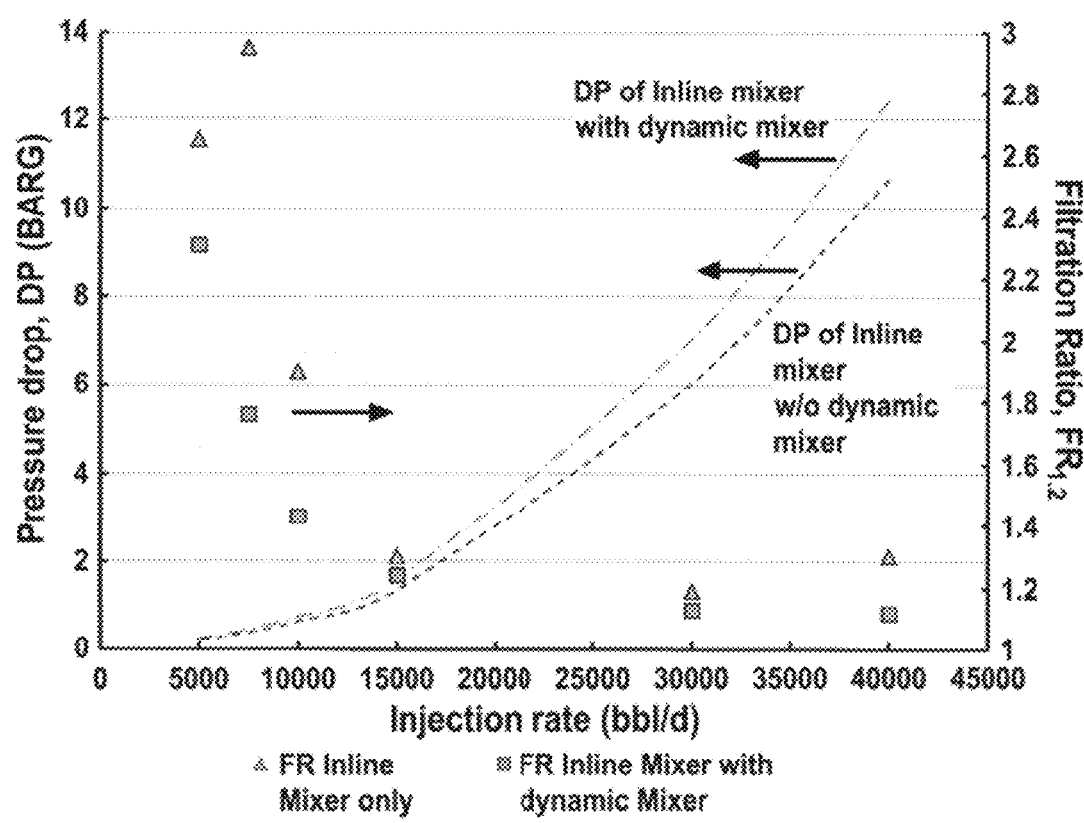
FIG. 6 is a plot showing the variation of pressure drop (DP) and filtration ratio (FR) as a function of injection rate using a mixer configuration at 2" yard test scale. Dotted lines indicate the DP across the static mixer with and without the dynamic mixer. Solids symbols indicate the filtration ratio of the aqueous polymer solutions at each corresponding injection rates. Filtration ratio was measured using 1.2 micron filter under 15 psi.

In some embodiments, the method can further comprise (f) comparing the property of the injection fluid measured in step (d) with a target value or range; and (g) altering the mixing of the injection fluid in step (c) to improve correlation between the property of the injection fluid measured in step (d) and the target value or range. By way of example, in certain embodiments, step (d) can comprise measuring a filter ratio of the injection fluid flowing through the fluid conduit using a portable apparatus in which the one or more analytical modules comprises a 1.2 micron filter having a diameter of 47 mm or 90 mm. In these embodiments, step (f) can comprise comparing the filter ratio of the injection fluid measured in step (d) the target value or range of 1.5 or less, and step (f) can comprise altering the mixing of the injection fluid in step (c) to reduce the filter ratio of the injection fluid to a value of 1.5 or less. Altering the mixing of the injection fluid in step (f) can comprise, for example, changing feedstock mixed to form the injection fluid, varying ratios of feedstock mixed to form the injection fluid, changing a mixer used to mix the injection fluid, or a combination thereof. In some embodiments, steps (d), (f), and optionally (g) are performed continuously Mixing Examples:

FIG. 6 shows that pressure drop (DP) and filtration ratio (FR) varied with injection rate when using a mixing process at 2" yard test scale. The dotted lines indicate the pressure drop (DP) across the static mixer with and without the dynamic mixer. Solids symbols indicate the filtration ratio of the inverted aqueous polymer solutions at each corresponding injection rate. Filtration ratio was measured at 1.2 micron filter under 15 psi. The mixing process also produced inverted aqueous polymer solutions that met the FR specification of ≤1.5 at an injection rate equivalent to ca. 30,000 bpd in a 6" system. This performance was sustained as the velocity across the mixers was reduced to the equivalent of 10,000 BPD.

Figure 7:
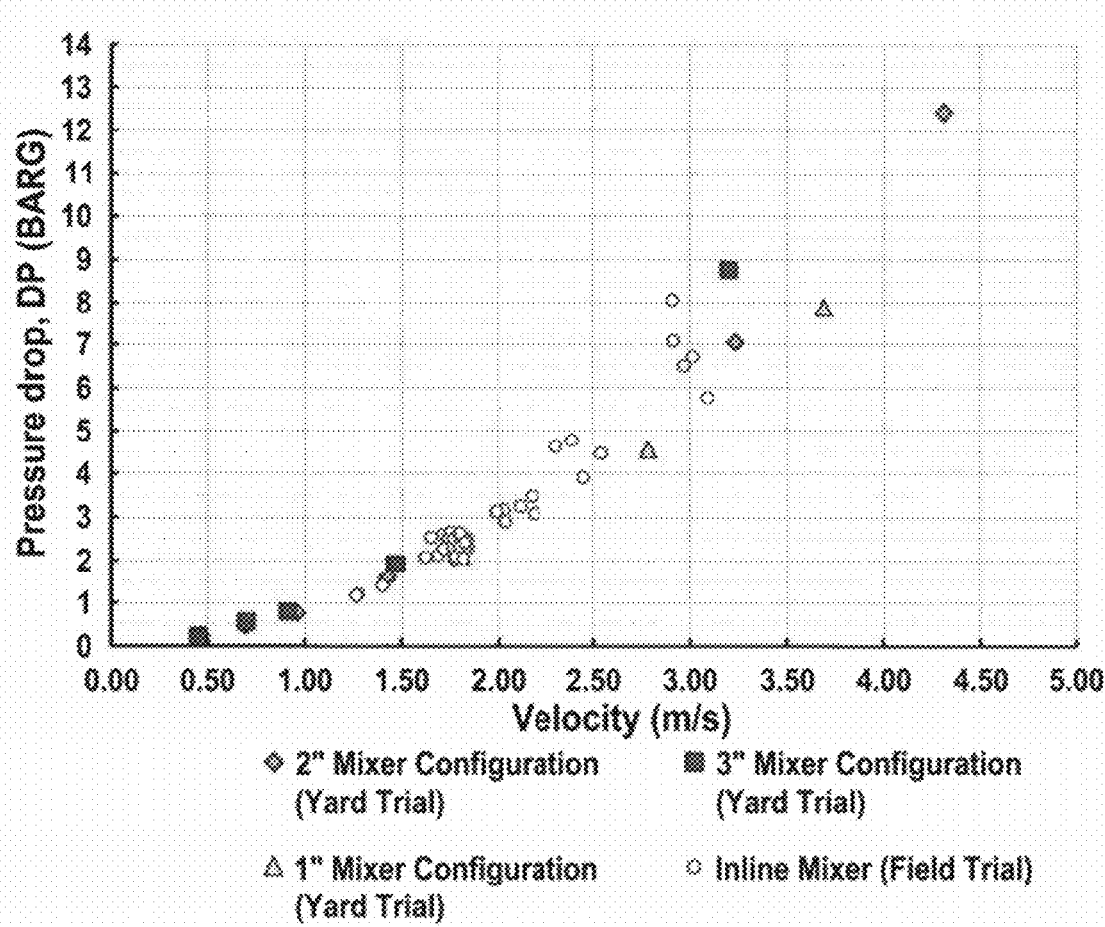
FIG. 7 is a plot showing the correlation between yard test and field scale DP as a function of fluid velocity.

FIG. 7 shows the relationship between DP and fluid velocity for the combined dynamic/static mixer configuration with 1", 2" and 3" units. The results associated with the three sizes show a strong correlation and demonstrate that a velocity of greater than ca. 1.0 m/s provides a minimum DP of ca. 1.0 bar over the two mixers.

Figure 8:
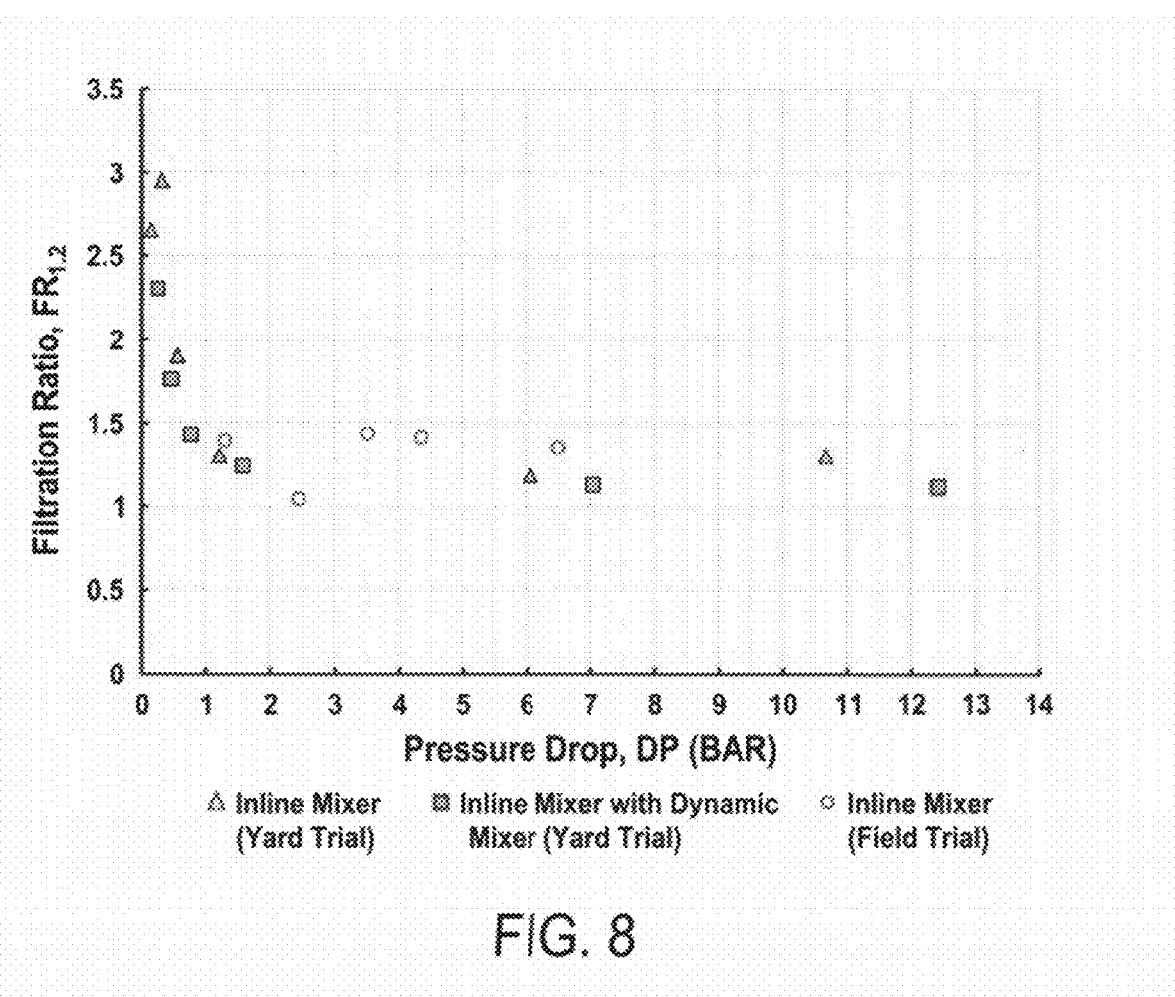
FIG. 8 is a plot showing the correlation between yard test and field scale FR as a function of DP.

FIG. 8 shows the relationship between DP and FR. Maintaining a DP of greater than 1 bar across the mixing configuration ensured that the <1.5 FR specification was met.

FIGS. 7 and 8 also demonstrate the impact of removing the dynamic mixer. At high flowrates, the impact is negligible but below ca. 12,500 bpd there was insufficient pressure drop to achieve the FR specification.

From the analysis above; it was concluded that, for the mixing process: (1) an FR of <1.5 could be achieved at a maximum injection solution velocity of 3.8 m/s to avoid excessive shearing; and (2) solution injection velocity could be maintained at >1.0 m/s to ensure sufficient mixing and achieve an FR≤1.5.

In addition to meeting key reservoir FR and viscosity specifications, the proposed mixing configuration proved robust in preventing mixer blockages. In an offshore environment, operational excursions leading to over injection of polyacrylamide can occur. Previous excursions in the oil field have led to plugging of the inversion mixer. Although, this plugging can be cleared by increasing water flow through the inversion mixer, there is no alternative routing available to prevent injection of the resulting highly concentrated polymer slug. Furthermore, installation of alternate disposal facilities is impractical.

In the yard environment, water injection rates equivalent to 5000 bpd were mixed with hPAM-based liquid polymer to form a ca. 7000 ppm solution. Even though the resulting solution failed to meet FR and viscosity specifications, no mixer blockages were observed.

Figure 9:
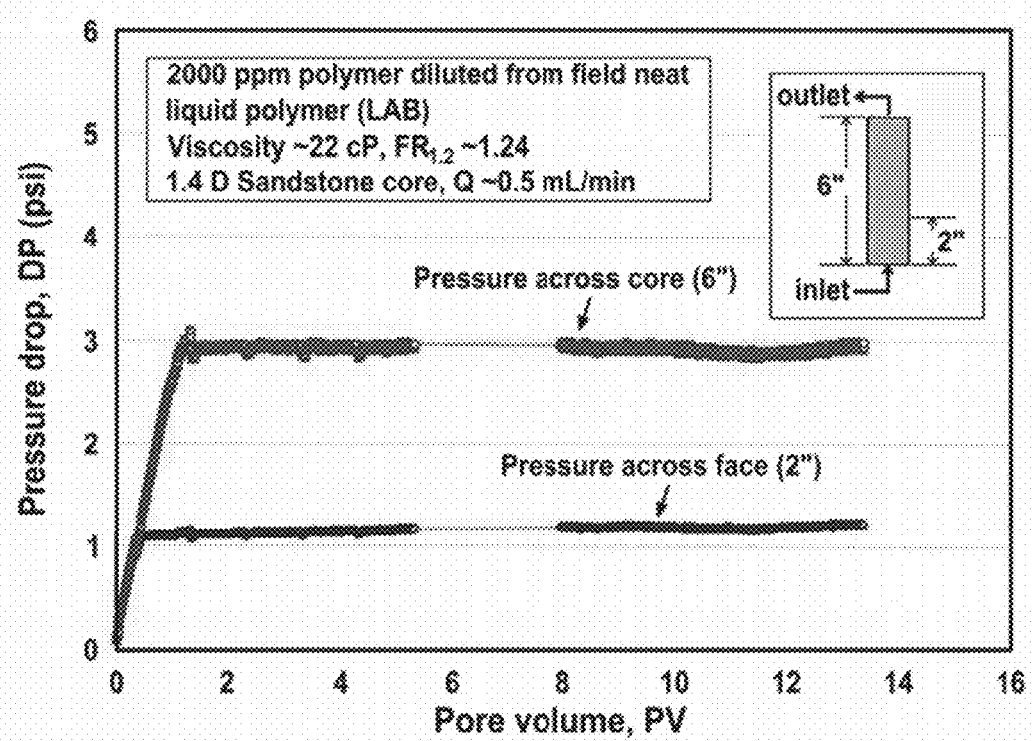
FIG. 9 is a plot of a field core flood (CF1) performed using the aqueous polymer solution in laboratory. Polymer was prepared in the lab using field neat liquid polymer. The polymer flood was run at 0.5 ml/min in the sandstone (1.4 D).

Example Performance of the Portable Apparatus in Hydrocarbon Field Tests:

One embodiment of the portable apparatus, including the external computing system, may be used to generate the data in FIG. 9. FIG. 9 shows a field core flood (CF1) using the field-prepared samples. Neat liquid polymer composition was collected in the tank and the inversion and dilution to 2000 ppm polymer solution was performed using the overhead mixer in the on-site laboratory. The viscosity and filtration ratio (FR) at 1.2 micron filter for the inverted aqueous polymer solution were found to be 22 cP and 1.24, respectively. The inverted aqueous polymer solution was injected at 0.5 mL/min into a 1.4 D sandstone core, and the pressure drop across the whole core (6") and injection face (2") were measured. The inverted aqueous polymer solution was prepared in the lab using neat liquid polymer. As shown in the FIG. 9, no significant plugging was observed during the coreflood up to 14 PV.

Figure 10:
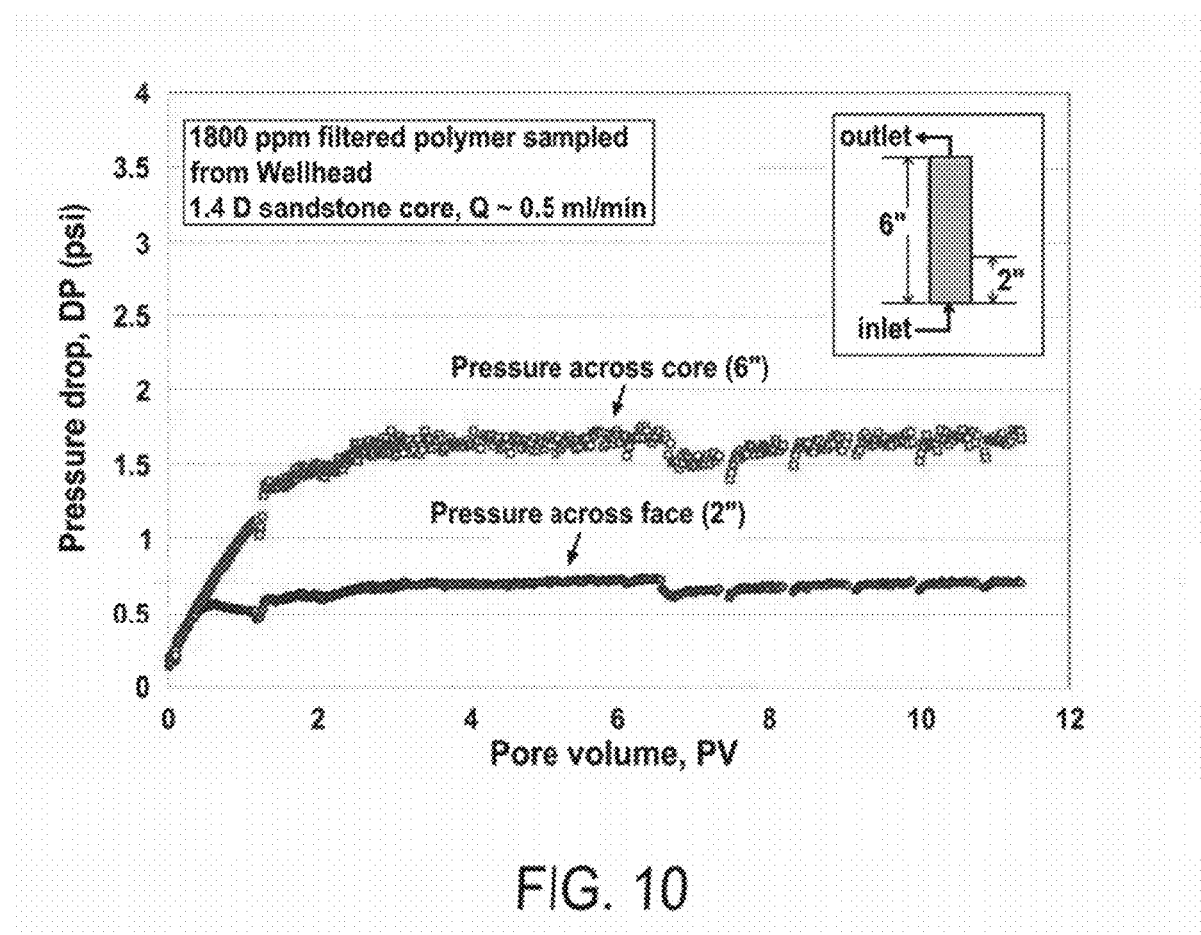
FIG. 10 is a plot of a field core flood (CF2) performed using aqueous polymer solution obtained from the wellhead. The LP composition was inverted using a single stage in-line mixer in the field, and a sample of the aqueous polymer solution was obtained from the wellhead. The polymer flood was run at 0.5 ml/min in the sandstone (1.4 D).

One embodiment of the portable apparatus, including the external computing system, may be used to generate the data in FIG. 10. FIG. 10 shows another example of field core flood (CF2) performed using a wellhead sample mixed in the field. The neat liquid polymer was inverted and diluted through the field inline mixer. The 1800 ppm inverted aqueous polymer solution sample was obtained from the wellhead. The polymer flood was run at 0.5 ml/min in the sandstone core (1.4 D). As shown in FIG. 10, no significant plugging was observed up to 11 PV, even though it took a little more to stabilize the pressure drop relative to trials performed using a lab-mixed aqueous polymer solution (see FIG. 9).

Figure 11:
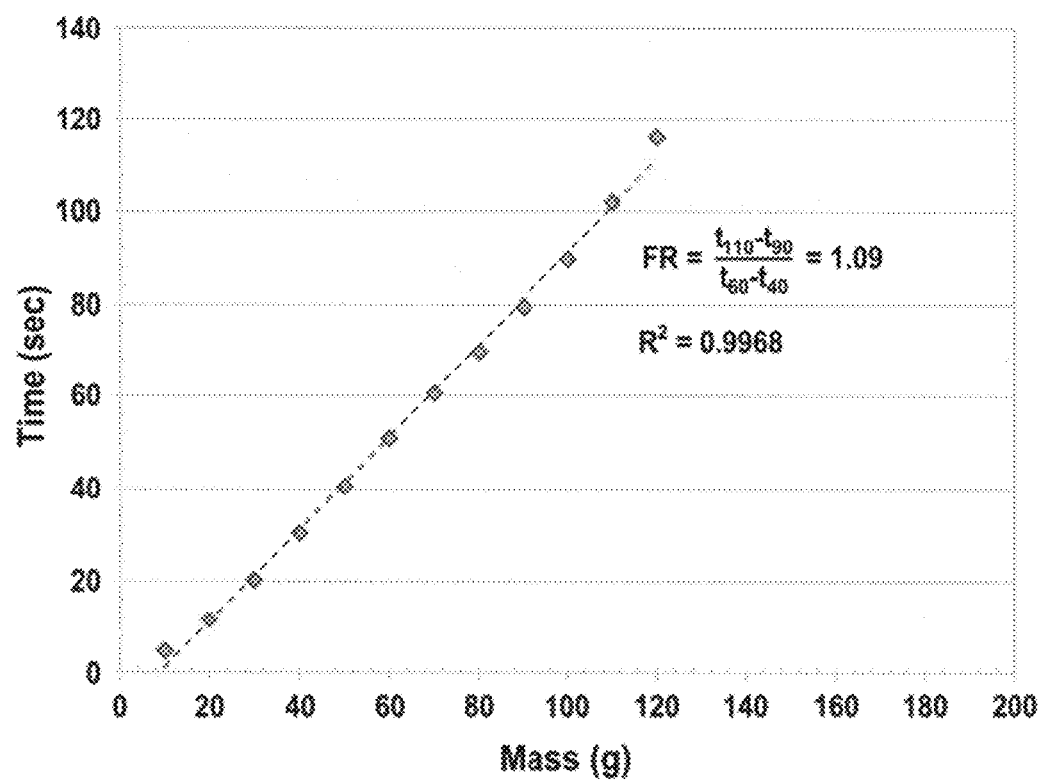
FIG. 11 shows the results of a filtration ratio test performed using samples of 1800 ppm aqueous polymer solution obtained from the wellhead. The filtration ratio test was performed using a 1.2 micron filter at 1 bar.

One embodiment of the portable apparatus, including the external computing system, may be used to generate the data in FIG. 11. FIG. 11 shows the filtration ratio test result at 1.2 micron under 1 bar for the wellhead-collected sample used for the CF2 flood. The sample exhibited very good filterability (FR of 1.09).

Figure 12:
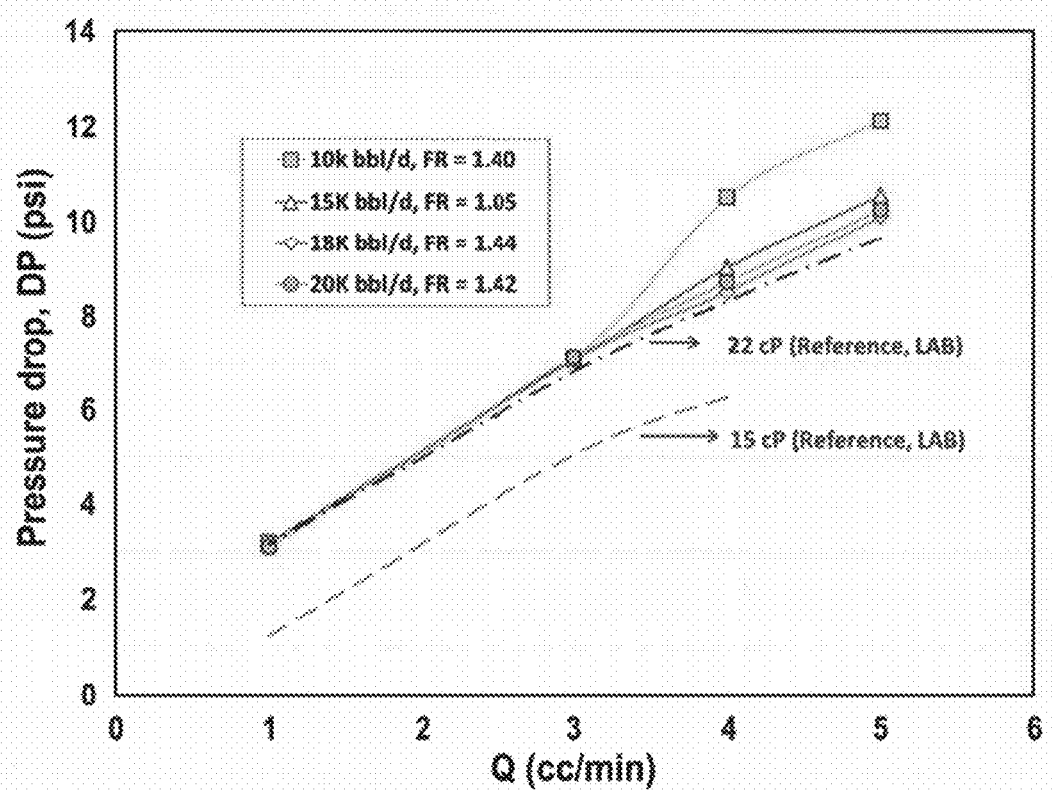
FIG. 12 is a plot of capillary viscosity measurements from an offshore field application showing the effect of changes in flow rate on coil viscometer measurements sampled from the wellhead. To estimate the viscosity of samples, pressure drop was measured through coil tubing on the core flood apparatus and data.

One embodiment of the portable apparatus, including the external computing system, may be used to generate the data in FIG. 12. FIG. 12 shows the pressure drop along different flow rate to estimate the viscosity using a capillary viscometer in a portable polymer flood box. As shown in the box, the field samples from wellhead exhibited comparable viscosities above the specified viscosity of 22 cP, which was measured in the laboratory as a reference. Filtration ratios of less than 1.5 were also observed a various different injection rates. These results indicate that the portable apparatus may be used to analyze filterability and viscosity yield of the injection fluid in the field.

Thus, various embodiments have been provided herein. In one embodiment, the portable apparatus for analyzing an injection fluid comprises a housing, wherein the housing comprises: at least one inlet to receive the injection fluid; at least one pre-filter coupled to the inlet to collect solids from the injection fluid, wherein at least one pressure transducer is coupled to the pre-filter for measuring a differential pressure across the pre-filter as the injection fluid flows through the pre-filter; at least one pressure vessel coupled to the pre-filter to deliver the injection fluid through at least one surrogate core for determining long term injectivity of the injection fluid, at least one capillary viscometer for determining viscosity of the injection fluid, at least one filter for determining a filter ratio of the injection fluid, at least one pH probe for determining pH of the injection fluid, at least one oxidation reduction potential probe for determining oxidation reduction potential of the injection fluid, at least one temperature probe for determining temperature of the injection fluid, at least one conductivity probe for determining conductivity of the injection fluid, or any combination thereof, wherein at least one pressure transducer is coupled to the surrogate core for determining a differential pressure across the surrogate core as the injection fluid flows through the surrogate core, wherein the surrogate core further includes at least one pressure tap for determining pressure across an injection face of the surrogate core, wherein at least one pressure transducer is coupled to the capillary viscometer for determining a differential pressure across the capillary viscometer as the injection fluid flows through the capillary viscometer, wherein at least one pressure transducer is coupled to the filter for determining an absolute pressure of the injection fluid to be filtered through the filter; at least one pump coupled to the pressure vessel to pump the injection fluid through the pressure vessel; and a power supply coupled to the pump and each pressure transducer to provide power to the pump and each pressure transducer.

In one example, the portable apparatus may be used to analyze an injection fluid that contains a polymer (and perhaps contains other components).

In one example, the portable apparatus may be used to analyze an injection fluid that contains produced fluid only.

The description and illustration of one or more embodiments provided in this application are not intended to limit or restrict the scope of the invention as claimed in any way. The embodiments, examples, and details provided in this disclosure are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope. For instance, such other examples are intended to be within the scope of the claims if they have structural or methodological elements that do not differ from the literal language of the claims, or if they include equivalent structural or methodological elements with insubstantial differences from the literal languages of the claims, etc. All citations referred herein are expressly incorporated herein by reference.

What is claimed is:

1. A portable apparatus for analyzing an injection fluid, the apparatus comprising a housing encompassing one or more components of the portable apparatus, wherein the components of the portable apparatus comprise:

an inlet to receive the injection fluid;
a pre-filter coupled to the inlet;
three analytical modules, wherein the three analytical modules comprise a surrogate core, a capillary viscometer, and a filter;
a pump coupled to the pre-filter to direct the injection fluid from the pre-filter through the three analytical modules;
one or more pressure transducers, wherein the one or more pressure transducers comprise a pressure transducer coupled to the pre-filter to measure a differential pressure of the injection fluid across the pre-filter, a pressure transducer coupled to the surrogate core to measure a differential pressure of the injection fluid across the surrogate core, a pressure transducer coupled to the capillary viscometer to measure a differential pressure of the injection fluid across the capillary viscometer, and a pressure transducer coupled to the filter to measure an absolute pressure of the injection fluid to be filtered through the filter;
a data acquisition system (DAS) that receives data from the one or more pressure transducers and calculates a property of the injection fluid from the data; and
a power supply coupled to the pump, the one or more pressure transducers, and the data acquisition system to provide power.

2. The apparatus of claim 1, wherein the one or more pressure transducers comprise a display providing a pressure reading.

3. The apparatus of claim 1, wherein one or more of the three analytical modules are each releasably connected to the portable apparatus.

4. The apparatus of claim 3, wherein one or more of the three analytical modules are each individually enclosed within the housing.

5. The apparatus of claim 1, wherein the pre-filter comprises a sand pack.

6. The apparatus of claim 1, wherein the DAS is coupled to an external computing system that receives data from the DAS and controls the pump.

7. The apparatus of claim 1, wherein the property of the injection fluid calculated from the data is chosen from an injectivity of the injection fluid for a minimum of 20 pore volumes and a maximum of 1,000 pore volumes, a viscosity of the injection fluid, a filter ratio of the injection fluid, or any combination thereof.

8. The apparatus of claim 7, wherein the filter ratio is 1.5 or less with a minimum of 1.0.

9. The apparatus of claim 1, further comprising a pressure vessel coupled to the pre-filter to receive and store injection fluid from the pre-filter and coupled to one or more of the three analytical modules to deliver the injection fluid from the pressure vessel to one or more of the three analytical modules, and wherein the pump is coupled to the pressure vessel to pump the injection fluid through the pressure vessel.

10. The apparatus of claim 1, wherein the components of the portable apparatus further comprise one or more additional analytical modules chosen from a temperature probe, a pH probe, a conductivity probe, an oxidation reduction potential probe, or any combination thereof.

11. The apparatus of claim 1, wherein the filter comprises a 1.2 micron filter having a diameter of 47 mm or 90 mm.

12. The apparatus of claim 1, wherein the components of the portable apparatus together form a path for fluid flow from the inlet to the one or more of the three analytical modules.

13. The apparatus of claim 1, wherein the portable apparatus of claim 1 is positioned for use on a tabletop.

14. A method for analyzing an injection fluid, the method comprising:
(a) providing a subsurface reservoir containing hydrocarbons there within;
(b) providing a wellbore in fluid communication with the subsurface reservoir;
(c) mixing an injection fluid and flowing the injection fluid through a fluid conduit to the wellbore;
(d) measuring a property of the injection fluid flowing through the fluid conduit using the portable apparatus of claim 1 having the three analytical modules that comprise the surrogate core, the capillary viscometer, and the filter, wherein the inlet of the portable apparatus is fluidly connected to the fluid conduit, thereby forming a path for fluid flow from the conduit to one or more of the three analytical modules in the portable apparatus; and
(e) injecting the injection fluid through the wellbore into the subsurface reservoir.

15. The method of claim 14, wherein the method further comprises:
(f) comparing the property of the injection fluid measured in step (d) with a target value or range; and
(g) altering the mixing of the injection fluid in step (c) to improve correlation between the property of the injection fluid measured in step (d) and the target value or range.

16. The method of claim 15, wherein step (d) comprises measuring a filter ratio of the injection fluid flowing through the fluid conduit using the portable apparatus of claim 1, wherein the filter comprises a 1.2 micron filter having a diameter of 47 mm or 90 mm;
wherein step (f) comprises comparing the filter ratio of the injection fluid measured in step (d) with the target value or range of 1.5 or less with a minimum of 1.0, and
wherein step (g) comprises altering the mixing of the injection fluid in step (c) to reduce the filter ratio of the injection fluid to a value of 1.5 or less with a minimum of 1.0.

17. The method of claim 16, wherein altering the mixing of the injection fluid in step (f) comprises changing feedstock mixed to form the injection fluid, varying ratios of feedstock mixed to form the injection fluid, changing a mixer used to mix the injection fluid, or a combination thereof.

18. The method of claim 16, wherein steps (d), (f), and optionally (g) are performed continuously.

19. The method of claim 14, wherein the injection fluid is analyzed for an enhanced oil recovery (EOR) operation chosen from a polymer flooding operation, an alkaline-polymer (AP) flooding operation, a surfactant-polymer (SP) flooding operation, an alkaline-surfactant-polymer (ASP) flooding operation, a conformance control operation, a hydraulic fracturing operation, or any combination thereof.

20. The method of claim 14, further comprises (h) recovering the hydrocarbons via a production wellbore in fluid communication with the subsurface reservoir.

\* \* \* \* \*